(12) United States Patent
Faulhaber

(10) Patent No.: US 10,842,539 B2
(45) Date of Patent: Nov. 24, 2020

(54) ORTHOPEDIC STABILIZATION DEVICES AND METHODS FOR INSTALLATION THEREOF

(71) Applicant: GLOBUS MEDICAL, INC., Audubon, PA (US)

(72) Inventor: Kurt Faulhaber, Renton, WA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 15/594,973

(22) Filed: May 15, 2017

(65) Prior Publication Data

US 2017/0245899 A1 Aug. 31, 2017

Related U.S. Application Data

(63) Continuation of application No. 14/515,602, filed on Oct. 16, 2014, now Pat. No. 9,681,897, which is a continuation of application No. 14/505,563, filed on Oct. 3, 2014, now Pat. No. 9,763,705.

(51) Int. Cl.
*A61B 17/70* (2006.01)
*A61F 2/44* (2006.01)
*A61F 2/30* (2006.01)

(52) U.S. Cl.
CPC ...... *A61B 17/7064* (2013.01); *A61B 17/7032* (2013.01); *A61B 17/7037* (2013.01); *A61B 17/7043* (2013.01); *A61B 17/7047* (2013.01); *A61B 17/7059* (2013.01); *A61B 17/7071* (2013.01); *A61F 2/4405* (2013.01); *A61F 2/447* (2013.01); *A61F 2/4455* (2013.01); *A61F 2002/3093* (2013.01); *A61F 2002/30153* (2013.01); *A61F 2002/30471* (2013.01); *A61F 2002/30578* (2013.01); *A61F 2002/30593* (2013.01); *A61F 2002/30733* (2013.01); *A61F 2002/30784* (2013.01); *A61F 2310/00359* (2013.01)

(58) Field of Classification Search
CPC ............................................. A61B 17/62–7071
See application file for complete search history.

(56) References Cited

U.S. PATENT DOCUMENTS

| | | | | | |
|---|---|---|---|---|---|
| 5,387,212 | A | * | 2/1995 | Yuan | A61B 17/701 606/264 |
| 5,437,669 | A | * | 8/1995 | Yuan | A61B 17/704 606/264 |
| 5,470,333 | A | * | 11/1995 | Ray | A61B 17/7055 606/261 |
| 5,582,612 | A | * | 12/1996 | Lin | A61B 17/7044 606/250 |
| 5,702,392 | A | * | 12/1997 | Wu | A61B 17/7008 606/250 |
| 6,458,131 | B1 | * | 10/2002 | Ray | A61B 17/7044 606/261 |
| 7,220,262 | B1 | * | 5/2007 | Hynes | A61B 17/7011 606/279 |
| 7,303,563 | B2 | * | 12/2007 | Poyner | A61B 17/7044 606/250 |

(Continued)

*Primary Examiner* — Nicholas J Plionis
*Assistant Examiner* — Steven J Cotroneo

(57) ABSTRACT

Embodiments herein are generally directed to spinal implants for use in orthopedic stabilization assemblies. In some embodiments, these implants may be used in conjunction with laminoplasty or laminectomy procedures.

19 Claims, 16 Drawing Sheets

(56) References Cited

U.S. PATENT DOCUMENTS

| | | | | |
|---|---|---|---|---|
| 9,585,697 B2* | 3/2017 | Stachniak | ........... | A61B 17/7035 |
| 2004/0162558 A1* | 8/2004 | Hegde | ................ | A61B 17/7044 |
| | | | | 606/287 |
| 2007/0055245 A1* | 3/2007 | Sasso | ................ | A61B 17/7064 |
| | | | | 606/278 |
| 2008/0021454 A1* | 1/2008 | Chao | ................ | A61B 17/7044 |
| | | | | 606/250 |
| 2008/0177314 A1* | 7/2008 | Lemoine | ........... | A61B 17/7055 |
| | | | | 606/250 |
| 2008/0281361 A1* | 11/2008 | Vittur | ................ | A61B 17/7052 |
| | | | | 606/249 |
| 2009/0093843 A1* | 4/2009 | Lemoine | ........... | A61B 17/7032 |
| | | | | 606/246 |
| 2010/0076493 A1* | 3/2010 | Fauth | ................ | A61B 17/1671 |
| | | | | 606/279 |
| 2010/0082067 A1* | 4/2010 | Kondrashov | ...... | A61B 17/7044 |
| | | | | 606/264 |
| 2010/0222779 A1* | 9/2010 | Ziemek | ............. | A61B 17/8042 |
| | | | | 606/71 |
| 2011/0190824 A1* | 8/2011 | Gephart | ................ | A61B 17/70 |
| | | | | 606/278 |
| 2014/0074166 A1* | 3/2014 | Scarrow | ............. | A61B 17/7067 |
| | | | | 606/247 |

\* cited by examiner

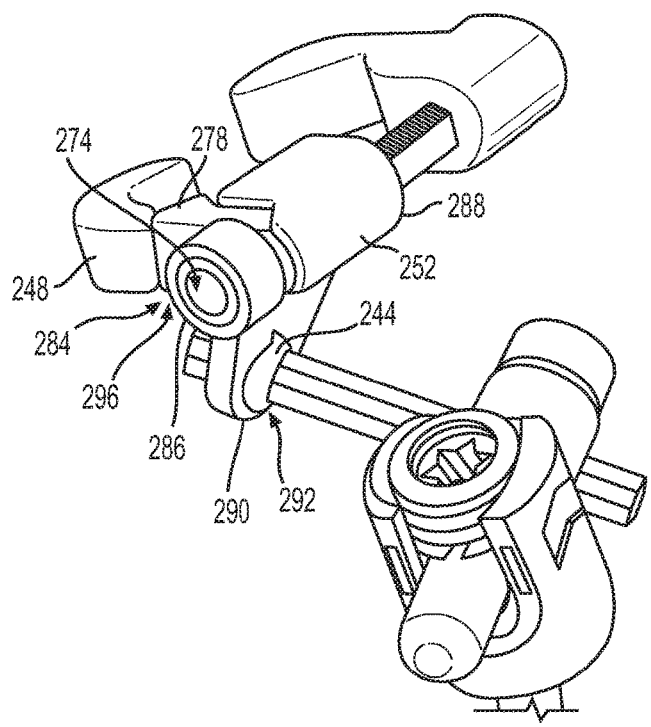
FIG. 6D
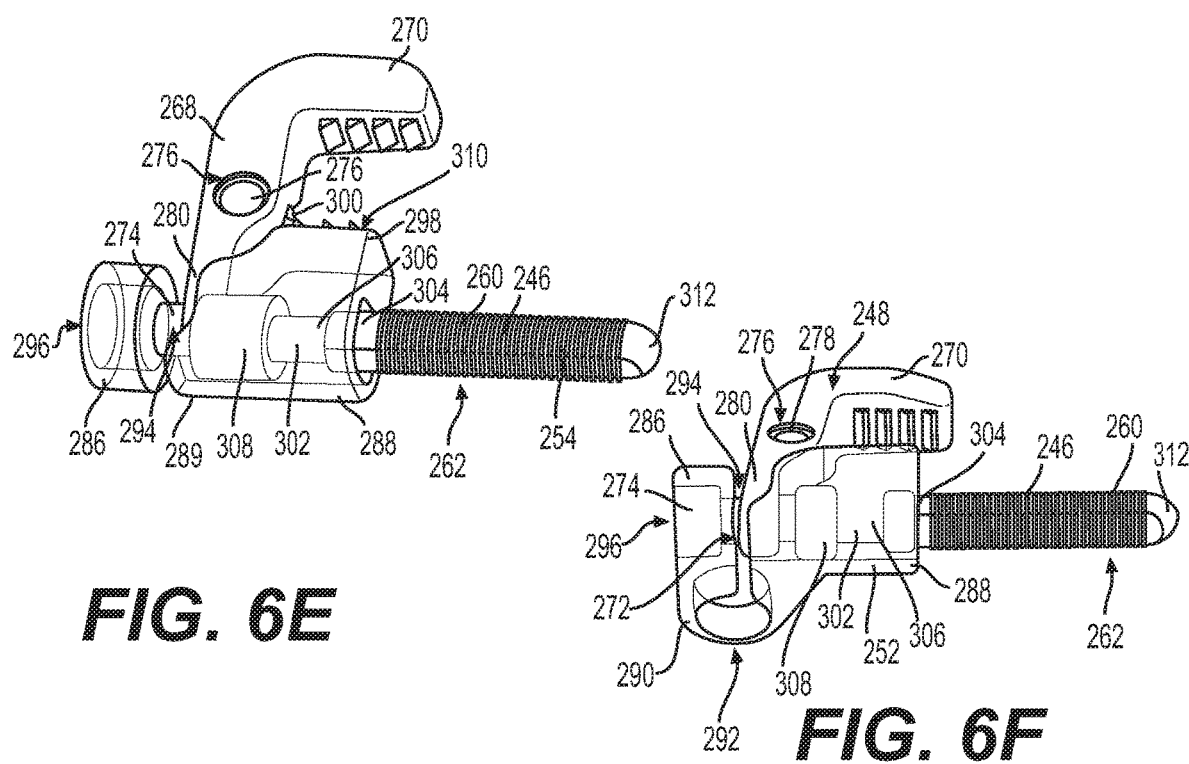
FIG. 6E
FIG. 6F

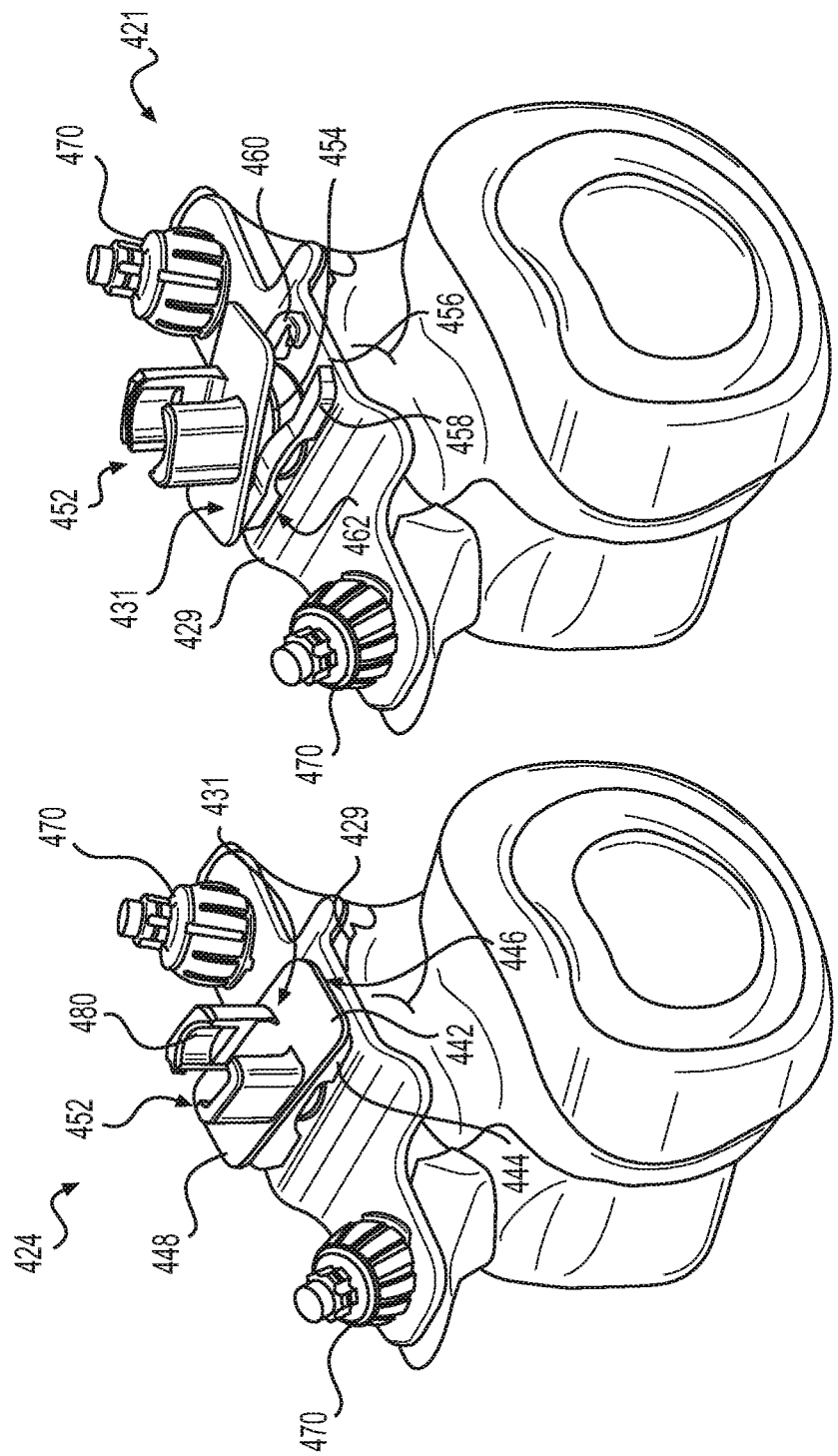

ORTHOPEDIC STABILIZATION DEVICES AND METHODS FOR INSTALLATION THEREOF

CROSS-REFERENCE TO RELATED APPLICATION

The present application is a continuation of U.S. patent application Ser. No. 14/515,602 filed on Oct. 16, 2014 which is a continuation of U.S. patent application Ser. No. 14/505,563, filed on Oct. 3, 2014, which is herein incorporated by reference in its entirety.

FIELD OF THE INVENTION

The present invention relates to orthopedic stabilization devices and methods used to install these devices.

BACKGROUND OF THE INVENTION

Many types of spinal irregularities can cause pain, limit range of motion, or injure the nervous system within the spinal column. These irregularities can result from, without limitation, trauma, tumor, disc degeneration, and disease. One example of a spinal irregularity is spinal stenosis, the narrowing of a spinal canal, which can result in the compression of spinal nerves such as the spinal cord or cauda equina. In turn, the nerve compression can result in pain, numbness, or weakness. Spinal stenosis may be caused by one or more conditions such as development of bone spurs, thickening of ligaments, fractures, and disc degeneration (e.g., due to arthritis).

Treatment of spinal stenosis can include, for example, a surgical procedure such as laminoplasty or laminectomy. Both of these procedures can involve expanding the spinal canal by modifying or removing the portion of a vertebra that may overlap the compressed nerve. In a laminoplasty procedure, a cut may be made through one lamina on a vertebrae and a hinge created on the other lamina, allowing a posterior section of the vertebrae to swing open to thereby enlarge the spinal canal. In a laminectomy procedure, both laminae and the spinous process may be removed. In either of these procedures, a variety of devices, such as rods, screws, cages, and/or plates, may be used to subsequently stabilize the spine.

SUMMARY OF THE INVENTION

Some embodiments herein are directed to a spinal implant that can include a first fixation section comprising a bottom surface configured to contact a first bone structure; a second fixation section comprising a bottom surface configured to contact a second bone structure; and a spacer section hingedly connected to the first and second fixation sections and configured for insertion between the first and second bone structures.

Other embodiments herein are directed to a spinal implant comprising a foldable sheet, wherein the foldable sheet can include a first fixation section configured to engage a first bone structure; a second fixation section configured to engage a second bone structure; a spacer section configured for insertion between the first and second bone structures; a first living hinge separating the first fixation section from the spacer section; and a second living hinge separating the second fixation section from the spacer section.

Yet other embodiments herein are directed to a spinal implant comprising a flat plate, wherein the flat plate can include a first fixation section configured to engage a first bone structure; a second fixation section configured to engage a second bone structure; and a spacer section hingedly coupled to the first and second fixation sections and configured for insertion between the first and second bone structures.

Other embodiments herein are directed to a method of installing a spinal implant assembly that can include providing a spinal implant assembly, comprising a spinal implant having a first fixation section, a second fixation section, and a spacer section hingedly connected to the first and second fixation sections, a first fixation member coupled with the first fixation section, and a second fixation member coupled with the second fixation section; assembling the spinal implant; inserting the spacer section between a first bone structure and a second bone structure; and coupling the first fixation section to the first bone structure and coupling the second fixation section to the second bone structure.

Some embodiments herein are directed to a spinal implant assembly that can include an anchor member; a translateral support member pivotably coupled to the anchor member; and a clamp member pivotably coupled to the translateral support member.

Other embodiments herein are directed to a method of installing a spinal implant assembly that can include providing a spinal implant assembly, comprising an anchor member, a translateral support member, and a clamp member; coupling the anchor member with a first bone structure; coupling the clamp member with a second bone structure; and locking the spinal implant assembly.

Some embodiments herein are directed to a spinal implant assembly that can include a superior translateral stabilization system; an inferior translateral stabilization system; and a secondary stabilization system configured to couple two adjacent vertebrae.

Other embodiments herein are directed to a spinal implant assembly that can include a superior translateral stabilization system comprising a first facet stabilization device and a first translateral plate; an inferior translateral stabilization system comprising a second facet stabilization device and a second translateral plate; and an intervertebral member configured to dynamically couple two adjacent vertebrae.

Yet other embodiments herein are directed to a spinal implant assembly that can include a superior translateral stabilization system comprising a first facet stabilization device and a first translateral plate; an inferior translateral stabilization system comprising a second facet stabilization device and a second translateral plate; and a secondary stabilization system configured to couple with the first and second translateral plates and configured to couple two adjacent vertebrae.

Other embodiments herein are directed to a spinal implant assembly that can include a superior translateral stabilization system comprising a first facet stabilization device and a first translateral plate; an inferior translateral stabilization system comprising a second facet stabilization device and a second translateral plate; and a secondary stabilization system comprising first and second bilateral members configured to couple two adjacent vertebrae.

Still other embodiments herein are directed to a method of installing a spinal implant assembly that can include providing a spinal implant assembly comprising a superior translateral stabilization system, an inferior translateral stabilization system, and a secondary stabilization system configured to couple two adjacent vertebrae; installing the superior translateral stabilization system; installing the inferior translateral stabilization system; and installing the secondary stabilization system.

Further areas of applicability of the present invention will become apparent from the detailed description provided hereinafter. It should be understood that the detailed description and specific examples, while indicating certain embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIGS. 6A-G illustrate one embodiment of a spinal implant assembly that includes a bone screw assembly;

FIGS. 8A-D illustrate embodiments of superior and inferior translateral stabilization systems of spinal implant assemblies described herein;

DETAILED DESCRIPTION

In a laminoplasty procedure, a spinal canal can be expanded by altering the laminar arch of a vertebra. In an "open door" procedure, a lamina on one side of a spinous process may be cut, and a lamina on the other side of the spinous process may be partially cut or grooved to develop a hinge, thereby allowing a posterior section of the vertebra to swing open and enlarge the spinal canal. The posterior section of the vertebra can be stabilized in an open position through a number of mechanisms. For example, a wedge or spacer made of allograft may be inserted into the gap between the two edges of the cut lamina and secured by a plate and/or bone screws. In some instances where an allograft spacer is used, it can be difficult to control the direction of bone regrowth. For example, new bone material may grow back towards the spinal canal, putting additional pressure on the spinal cord and/or reducing the efficacy of the procedure. Accordingly, disclosed herein are new and improved spinal implants and assemblies that can encourage controlled bone growth. Also described herein are new and improved spinal implants and assemblies that can stabilize a spine, post-laminoplasty, in an open configuration and without the use of a wedge or spacer.

Components of all of the spinal stabilization devices disclosed herein can be made of materials known to those skilled in the art, including metals (e.g., titanium), metal alloys, polymers (e.g., poly ether ether ketone (PEEK), polyphenylene sulfone (PPSU), polysulfone (PSU), polycarbonate (PC), polyetherimide (PEI), polypropylene (PP), polyacetals, or mixtures or co-polymers thereof), allograft, and/or combinations thereof. The components can also be machined and/or manufactured using techniques known to those skilled in the art. For example, polymeric components may be injection-molded or blow-molded.

Figure 1A:
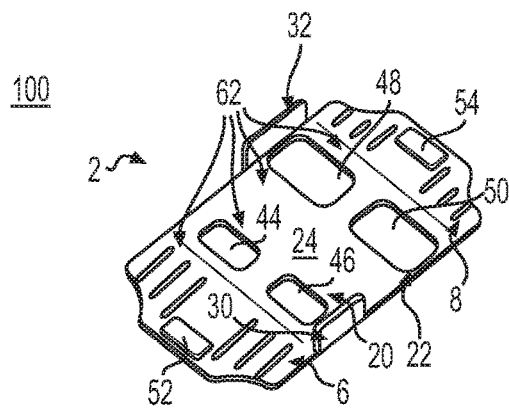
FIGS. 1A-D illustrate perspective views of a spinal implant assembly as described herein.
Figure 1B:
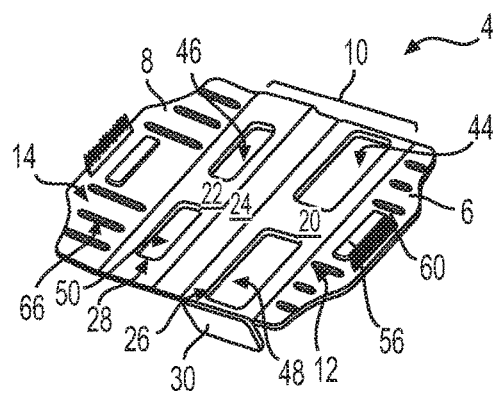
Figure 1C:
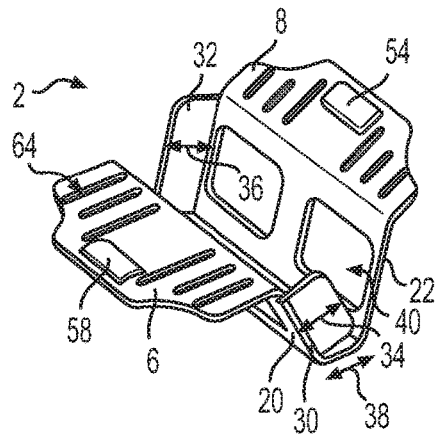
Figure 1D:
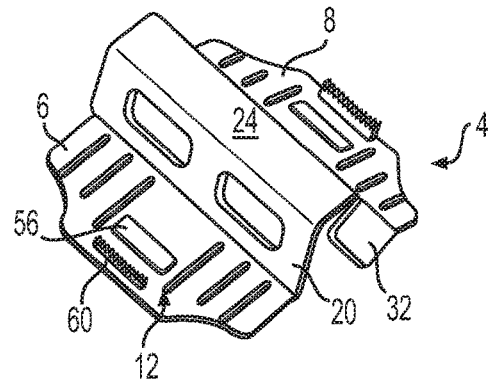

Turning now to FIGS. 1A-D, four views of a spinal implant 100 are illustrated in accordance with embodiments described herein. FIGS. 1A and 1C illustrate a top surface 2 of the spinal implant 100, and FIGS. 1B and 1D illustrate a bottom surface 4 of the spinal implant 100. FIGS. 1A-B illustrate a generally flat, unfolded, or unassembled configuration of the spinal implant 100 (e.g., unfolded with the exception of the first and second end walls), and FIGS. 1C-D illustrate a folded or assembled configuration of the spinal implant 100.

Figure 3:
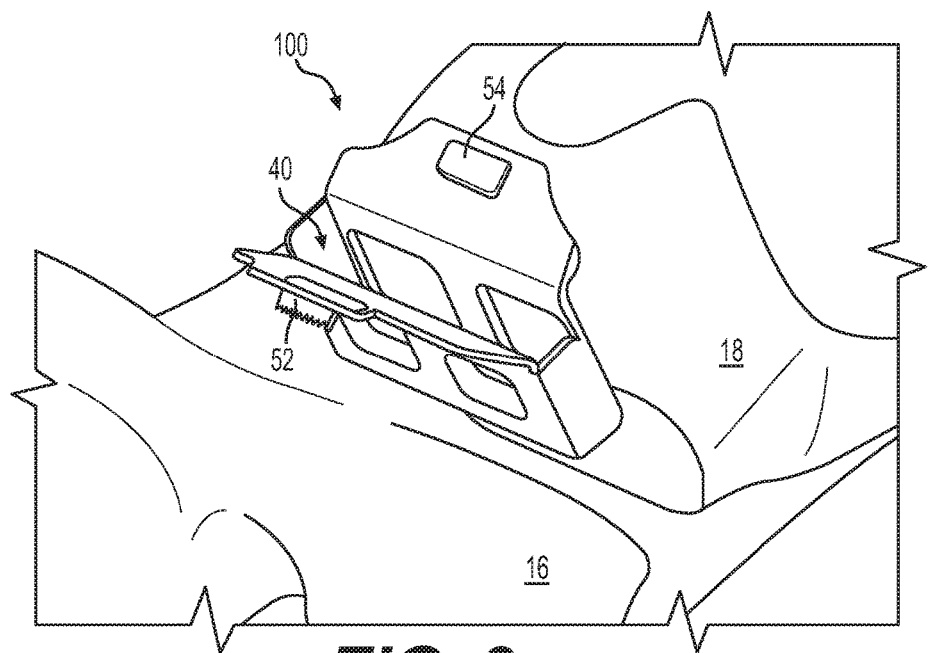
FIG. 3 illustrates the insertion of a spinal implant assembly between first and second bone structures.

As illustrated in FIGS. 1A-D, the spinal implant 100 can include a first fixation section 6, a second fixation section 8, and a spacer section 10. The first fixation section 6 can include a bottom surface 12. The bottom surface 12 can be configured to contact a first bone structure, such as a first section of a lamina 16, as illustrated in FIG. 3. The second fixation section 8 can also include a bottom surface 14. The bottom surface 14 can be configured to contact a second bone structure, such as a second section of a lamina 18, as illustrated in FIG. 3. As illustrated in FIGS. 1A-D, the first and second fixation sections 6, 8 can each include at least one elongate slot 64, 66. Each elongate slot can pass through from the top surface to the bottom surface of the fixation section. In some embodiments, the first and second fixation sections 6, 8 can each include a plurality of elongate slots. Advantageously, the elongate slots can be filled with bone growth material and can enhance and/or promote the fusion of the spinal implant 100 to a vertebra. Additionally, the elongate slots can allow the first and second fixation sections 6, 8 to be flexible, thereby easing the implantation process and/or promoting a close fit with the first and second bone structures 16, 18.

The spacer section 10 can be disposed between and connected to the first fixation section 6 and the second fixation section 8. In some embodiments, the spacer section 10 can be pivotably or hingedly connected to the first and second fixation sections 6, 8. The spacer section 10 can be configured for insertion between the first and second bone structures (e.g., between two sections of a lamina, such as first lamina section 16 and second lamina section 18). The spacer section 10 can also be configured to distract the first and second bone structures.

In some embodiments, the spacer section 10 can include a first support wall 20, a second support wall 22, and a base wall 24. The first support wall 20 can be pivotably or hingedly connected to the first fixation section 6. Additionally, the first support wall 20 can include a bottom surface 26. The bottom surface 26 can be configured to contact a first bone structure, such as the first section of the lamina 16, as illustrated in FIG. 3. The second support wall 22 can also include a bottom surface 28. The bottom surface 28 can be configured to contact a second bone structure, such as the second section of the lamina 18, as illustrated in FIG. 3. In some embodiments, at least one of the first and second support walls 20, 22 can include at least one hole or window passing therethrough from a top surface to the bottom surface 26, 28. As illustrated in FIG. 1A, the first support wall 20 can include two holes 44, 46. Additionally, the second support wall 22 can include two holes 48, 50. The holes can be of the same or different sizes. The holes can also have a variety of different shapes, such as round, oval, rectangular, and/or rectangular with rounded edges. Advantageously, the holes can be configured to promote bone growth and fusion.

The base wall 24 can be disposed between and pivotably or hingedly connected to the first and second support walls 20, 22. In contrast with the first and second support walls 20, 22, the base wall 24 may be solid, e.g., it may not include any holes to promote bone growth and/or fusion. The base wall 24 can have a width 38, as illustrated in FIG. 1C. As illustrated in FIG. 1A, the spacer section 10 can further include a first end wall 30 and a second end wall 32. The first end wall 30 can be pivotably or hingedly connected to the first support wall 20. The second end wall 32 can be pivotably or hingedly connected to the second support wall 22. The first and second end walls 30, 32 can each have a width 34, 36, as illustrated in FIG. 1C. In some embodiments, the widths 34, 36 of the first and second end walls 30, 32 can be equal. In other embodiments, the widths 34, 36, 38 of the first end wall 30, second end wall 32, and base wall 24 can all be equal.

Figure 5A:
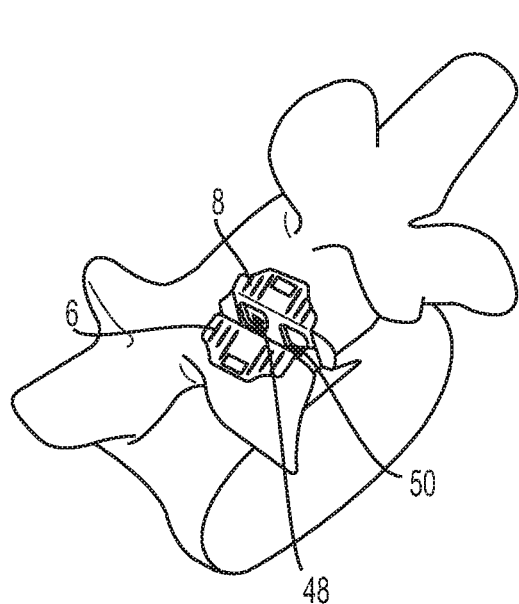
FIGS. 5A-B illustrate insertion of bone graft material into a spinal implant assembly.
Figure 5B:
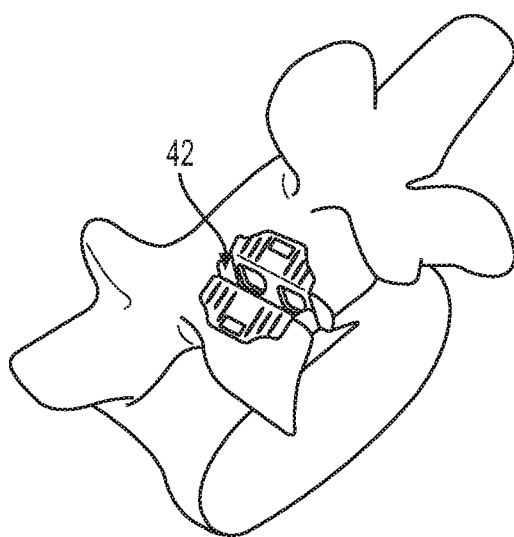

As illustrated in FIGS. 1C and 3, for example, the spacer section 10 can be configured to form a cavity 40. The cavity 40 can be in the shape of a hexahedron having five walls (defined by the first support wall 20, second support wall 22, base wall 24, first end wall 30, and second end wall 32) and one open end. In some embodiments, the cavity 40 can be configured to receive bone graft or growth-promoting material 42 through the open end, as illustrated in FIG. 5B. Any suitable bone graft or growth-promoting material may be inserted, such as allograft bone, autograft bone, demineralized bone matrix, calcium phosphates such as hydroxyapatite (HA) and tricalcium phosphate, human growth factor, bone morphogenetic proteins, steroids, stem cells, or combinations thereof. Advantageously, the cavity 40 of spinal implant 100 may provide greater flexibility as compared to other implants, such as those that include a solid allograft spacer. For example, the combinations and/or amounts of bone graft or growth-promoting materials can be varied to provide individualized treatment for a patient. Additionally, in some embodiments, all of the walls of the cavity 40, except for the base wall 24, may include a hole or window. In these embodiments, bone growth may advantageously be promoted in all directions except in a direction towards the spinal canal.

Some embodiments herein are directed to a spinal implant assembly, which can include the spinal implant 100 coupled with one or more fixation members. For example, the spinal implant assembly can include the spinal implant 100 coupled with a first fixation member 52 and a second fixation member 54, as illustrated in FIGS. 1A-D. The first and second fixation members 52, 54 can be configured to anchor the first and second fixation sections 6, 8 to the first and second bone structures 16, 18. Accordingly, one or both of the first and second fixation members 52, 54 can include a bone-engaging projectile. As illustrated in FIGS. 1A-D, one or both of the first and second fixation members 52, 54 can be a staple. Advantageously, a staple may have a greater surface area over which its load may be distributed, as compared to other types of fasteners, and may therefore be more efficient. Accordingly, the size of the staples used in embodiments herein may be smaller than the size of other types of fasteners that might be needed to provide similar stability, thereby reducing risk to the patient. This can be of importance in areas such as the lamina, where the bone may be naturally thin and/or delicate. Regardless, in other embodiments, one or both of the first and second fixation members 52, 54 can be a screw, nail, or other type of fastener. The first and second fixation members 52, 54 may be made from any suitable biocompatible materials. In some embodiments, the first and second fixation members 52, 54 may be made of a metal, such as titanium or alloys thereof, or a shape-memory metal, such as nitinol. As illustrated in FIGS. 1B-C, the first fixation member 52 can include a crown 56, a body 58 extending from the crown 56, and teeth 60 extending from the body 58. The teeth 60 can be sharpened and/or serrated to advantageously assist with engagement of or penetration into the bone structure. The second fixation member 54 can also include some or all of the features described herein with respect to the first fixation member 52.

In some embodiments, the first fixation section 6 can include one or more receptacles for receiving the first fixation member 52 therein. For example, the first fixation section 6 can include two slots, such as a lateral slot and a medial slot. The body 58 of the first fixation member 52 may be oriented on a top surface of the first fixation section 6 between the two slots, as illustrated in FIG. 1C. The teeth 60 may pass through the lateral slot to the bottom surface 12, as illustrated in FIG. 1D. The crown 56 may pass through the medial slot and may be bent or angled to lie generally flat along the bottom surface 12, as further illustrated in FIG. 1D. Advantageously, in some embodiments, the first fixation member 52 may be removable. Those skilled in the art may appreciate that a firm and/or permanent fixation between the first fixation member 52 and first fixation section 6 may not be needed because the resulting bone growth can advantageously couple the two pieces together. However, in other embodiments, the first fixation member 52 may be affixed (e.g., welded or bonded) to the first fixation section 6. In yet other embodiments, the first fixation member 52 may be an extension of the first fixation section 6, as opposed to being a separate member.

As described herein, the spinal implant 100 can have one or more sections or segments that are rotatably, pivotably, and/or hingedly coupled or connected to one another. Any type and/or combination of bearings or hinges known in the art may be used. As illustrated in FIG. 1A, for example, the spinal implant 100 can include one or more living hinges 62 (e.g., a hinge made from the same material as the sections it connects, and which may include a thinned section or groove). In some embodiments, all of the sections or segments that are pivotably and/or hingedly coupled may be coupled using living hinges. In these embodiments, the spinal implant 100 may be foldable, flexible, and/or bendable, as it may be configured to bend or flex along the living hinges. Advantageously, in embodiments including living hinges, the spinal implant 100 may be a monolithic device formed from a single piece of material (e.g., PEEK or other polymer). When a plastic is used, the spinal implant 100 may be manufactured using an injection-molding procedure.

In some embodiments, the spinal implant 100 may be referred to as a foldable sheet. In these embodiments, the spinal implant 100 may include a generally thin, flat piece of material (e.g., plastic or metal) that can be folded along one or more grooves or thinned sections. Those skilled in the art may appreciate that each groove may be configured to act as a living hinge. Similarly, in other embodiments, the spinal implant 100 may be referred to as a flat plate. In these embodiments, the spinal implant 100 can also include a generally thin, flat piece of material (e.g., plastic or metal). The flat plate may have one or more sections or segments that are rotatably, pivotably, and/or hingedly coupled or connected to one another via living hinges or other hinges as described herein. Those skilled in the art may appreciate that the foldable sheets and flat plates described herein may include any or all of the features described with respect to the spinal implant 100 in general.

In use, the spinal implant assembly may begin with the spinal implant 100 in a flat (e.g., unfolded and/or unassembled) configuration and the first and second fixation members 52, 54 coupled with the first and second fixation sections (e.g., placed in the lateral and medial slots). To assemble the spinal implant, the first and second end walls 30, 32 may be rotated or pivoted (e.g., folded along the living hinges) approximately 90 degrees towards the top surface 2 of the spinal implant 100, as illustrated in FIGS. 1A-B. As illustrated in FIGS. 1C-D, the first and second support walls 20, 22 may be rotated or pivoted (e.g., folded along living hinges 62a) approximately 90 degrees towards the top surface 2 of the spinal implant 100. Further, as illustrated in FIGS. 1C-D, the first and second fixation sections 6, 8 may be rotated or pivoted approximately 90 degrees in the opposite direction, toward the bottom surface 4 of the spinal implant 100. Examples of the spinal implant 100 in an assembled, folded configuration are illustrated in FIGS. 3-5B. Those skilled in the art may appreciate that the steps of assembling the spinal implant 100 with regards to pivoting the various sections can occur in any order.

Figure 2:
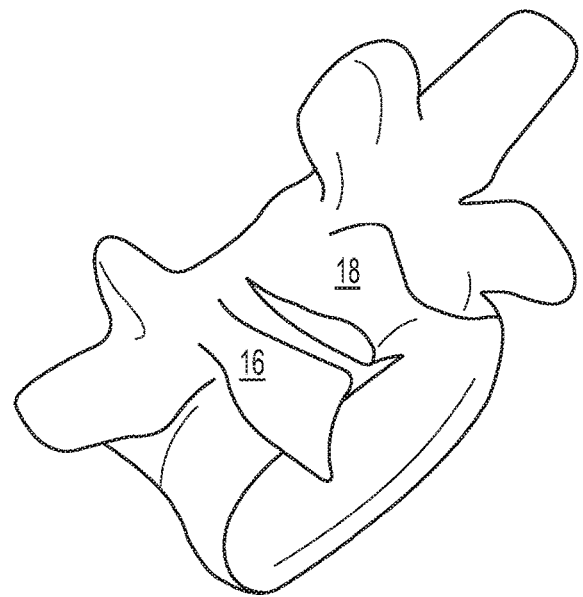
FIG. 2 illustrates one method of performing a laminoplasty procedure.
Figure 4A:
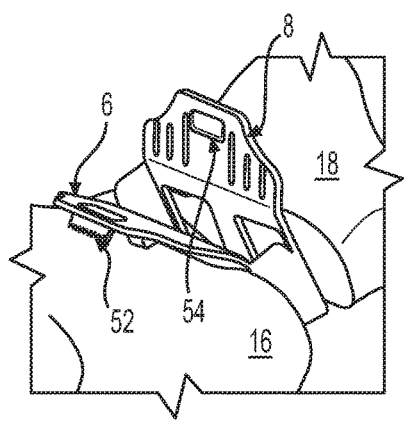
FIGS. 4A-C illustrate the fastening of a spinal implant assembly to first and second bone structures.
Figure 4B:
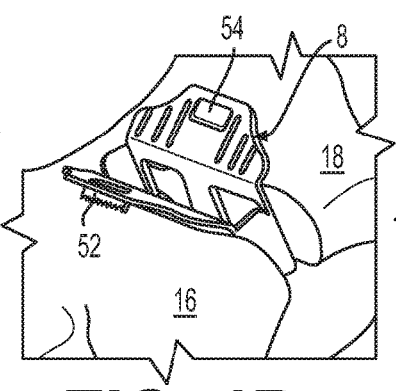
Figure 4C:
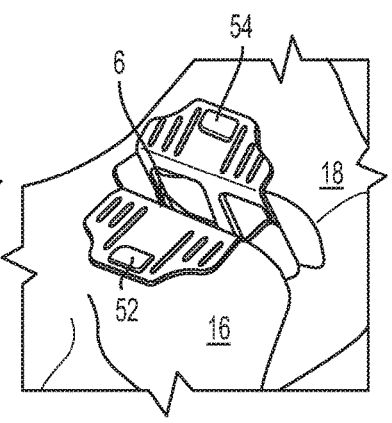

A laminoplasty procedure can be performed in accordance with standard techniques known to those of skill in the art. As illustrated in FIG. 2, a lamina (e.g., a left lamina) can be completely cut, resulting in the first and second bone structures 16, 18, illustrated in FIG. 3. Another lamina (e.g., a right lamina) can be scored or partially cut to create a hinge. The posterior section of the vertebrae may pivot outwards via the hinge, enlarging the spinal canal and creating a gap between the first and second bone structures, 16, 18. As illustrated in FIG. 3, the spinal implant assembly (e.g., the spinal implant 100 and first and second fixation members 52, 54) can be implanted, with the assembled spacer section 10 inserted between the first and second bone structures 16, 18. After insertion, the first and second fixation sections 6, 8 may be coupled or fastened to the first and second bone structures 16, 18 via the first and second fixation members 52, 54. As illustrated in FIGS. 4A-C, the first and second fixation members 52, 54 may be inserted into the first and second bone structures 16, 18. As illustrated in FIG. 5B, bone graft material 42 may be placed into the cavity 40. Advantageously, the spinal implant 100 may have one or more graft windows (e.g., holes 48, 50) that can encourage or promote bone growth and/or fusion, as illustrated in FIG. 5A.

Turning now to FIGS. 6A-G, a spinal implant assembly 200 is illustrated in accordance with embodiments described herein. The spinal implant assembly 200 can include an anchor member (e.g., bone screw assembly 202 or plate assembly 312), a translateral support member 204, and a clamp member 206. The translateral support member 204 may be pivotably coupled to both the anchor member and the clamp member 206. In some embodiments, the translateral support member 204 may be pivotably coupled to the anchor member and/or the clamp member 206 through one or more variable angle joints.

The anchor member can be configured to anchor or fasten the spinal implant assembly 200 to a first bone section. For example, in an embodiment where a left lamina is transected as part of an open door laminoplasty, the anchor member can anchor or fasten the spinal implant assembly 200 to a left section of the transected lamina. In some embodiments, the anchor member can engage a pedicle of the first bone section. The anchor member can include any suitable fastener(s) known in the art. For example, in some embodiments, the anchor member can include a bone screw, such as a pedicle screw. The pedicle screw can be configured for polyaxial or monoaxial movement. The anchor member can also include one or more coupling members that can be configured to couple the fastener to the translateral support member. For example, in some embodiments, the anchor member can include a tulip-head housing. In other embodiments, the anchor member can include a plate.

Figure 6A:
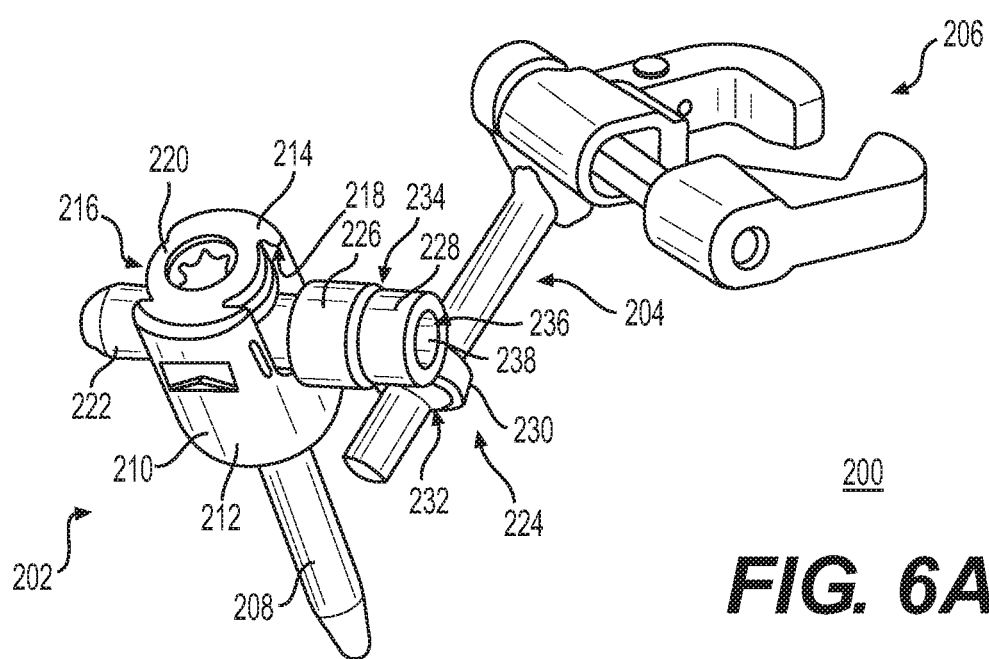

One example of an anchor member in accordance with the embodiments described herein is illustrated in FIG. 6A. In this embodiment, the anchor member can include a bone screw assembly 202. The bone screw assembly 202 can include a fastener member 208. The fastener member 208 can include an elongate, threaded body extending from an enlarged, rounded head. In some embodiments, the fastener member 208 can be a polyaxial pedicle screw. The bone screw assembly 202 can also include a housing member 210. The housing member 210 can include a lower portion 212 and an upper portion 214. The lower portion 212 can be configured to receive the head of the fastener member 208. The upper portion 214 can include a rod-receiving channel 216 and an internally-threaded section 218. The internally-threaded section 218 can be configured to mate with a set screw 220, which can optionally be included in the bone screw assembly 202. In some embodiments, the bone screw assembly 202 can additionally include a coupling member configured to rest atop or around the head of the fastener member 208, within the housing member 210. The coupling member may be configured to assist with locking the fastener member 208 at a particular angle with respect to the housing 210 and/or rod 222.

As illustrated in FIG. 6A, the bone screw assembly 202 can also include a rod 222. The rod 222 can include a first locking member 224. The first locking member 224 can be configured to receive at least a portion of the translateral support member 204, such as the first enlarged member 242, described further herein. As illustrated in FIG. 6A, the first locking member 224 can be disposed on one end of the rod 222 and can include a first, inner ring 226, a second, outer ring 228, and a collar 230 that connects or joins the first and second rings 226, 228. The first and second rings 226, 228 can be separated by a gap 234. The collar 230 may have a rounded, partially rounded, spherical, partially spherical, spheroidal, or partially spheroidal inner surface defining a conduit 232. The conduit 232 may extend through the collar 230 and may be configured to receive the portion of the translateral support member 204 (e.g., first enlarged member 242, described further herein). The conduit 232 can be in fluid communication with the gap 234. The first locking member 224 can also include an internally-threaded bore 236. The internally-threaded bore 236 can pass through at least a portion of the first and/or second rings 226, 228, and can share a longitudinal axis with that of the rod 222. The bone screw assembly 202 can optionally include an externally-threaded first securing element 238, which may be configured to be received within the internally-threaded bore 236 of the first locking member 224.

Figure 6B:
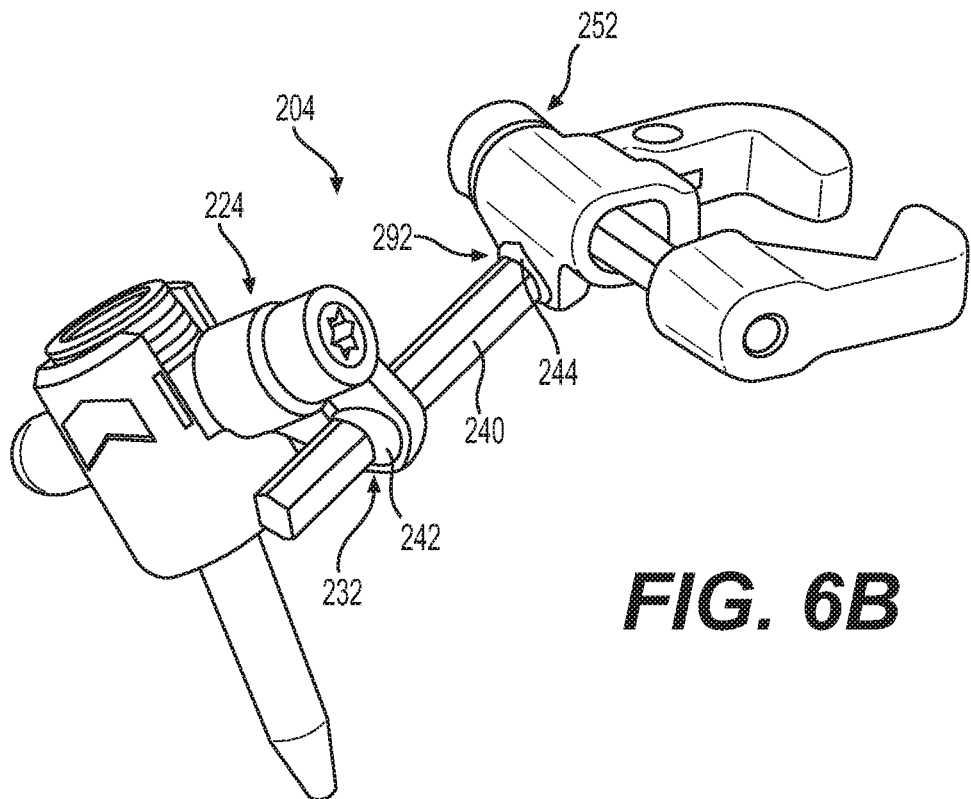

As illustrated in FIG. 6B, the translateral support member 204 can include an elongate rod 240. The rod 240 can include a first end having a first enlarged member 242. In some embodiments, the rod 240 may also include a second end having a second enlarged member 244. At least one of the first and second enlarged members 242, 244 may include a rounded, spherical, or spheroidal shape. Additionally, the first and/or section enlarged members 242, 244 may have a diameter that is greater than a diameter of the elongate rod 240. The first enlarged member 242 may be configured to nest in the conduit 232 of the first locking member 224. The second enlarged member 244 may be configured to nest in the conduit 292 of the second locking member 252, discussed further herein. In some embodiments, the first enlarged member 242 may have a diameter that is greater than or equal to a diameter of the conduit 232. The second enlarged member 244 may also have a diameter that is greater than or equal to a diameter of the conduit 292.

As illustrated in FIGS. 6C-F, the clamp member 206 can include a clamp rod 246, an extension member 302, a first articulating jaw 248, a second translating jaw 250, a second locking member 252, and a second securing element 274. In some embodiments, the clamp member 206 may be described as having a first half and a second half, wherein the first half includes the clamp rod 246, extension member 302, first articulating jaw 248, second locking member 252, and second securing element 274, and the second half includes the second locking member 252. The first articulating jaw 248, second translating jaw 250, and/or second locking member 252 may be disposed on the clamp rod 246. In some embodiments, the first articulating jaw 248, second translating jaw 250, and/or second locking member 252 can each include a bore configured to receive the clamp rod 246 therethrough.

Figure 6C:
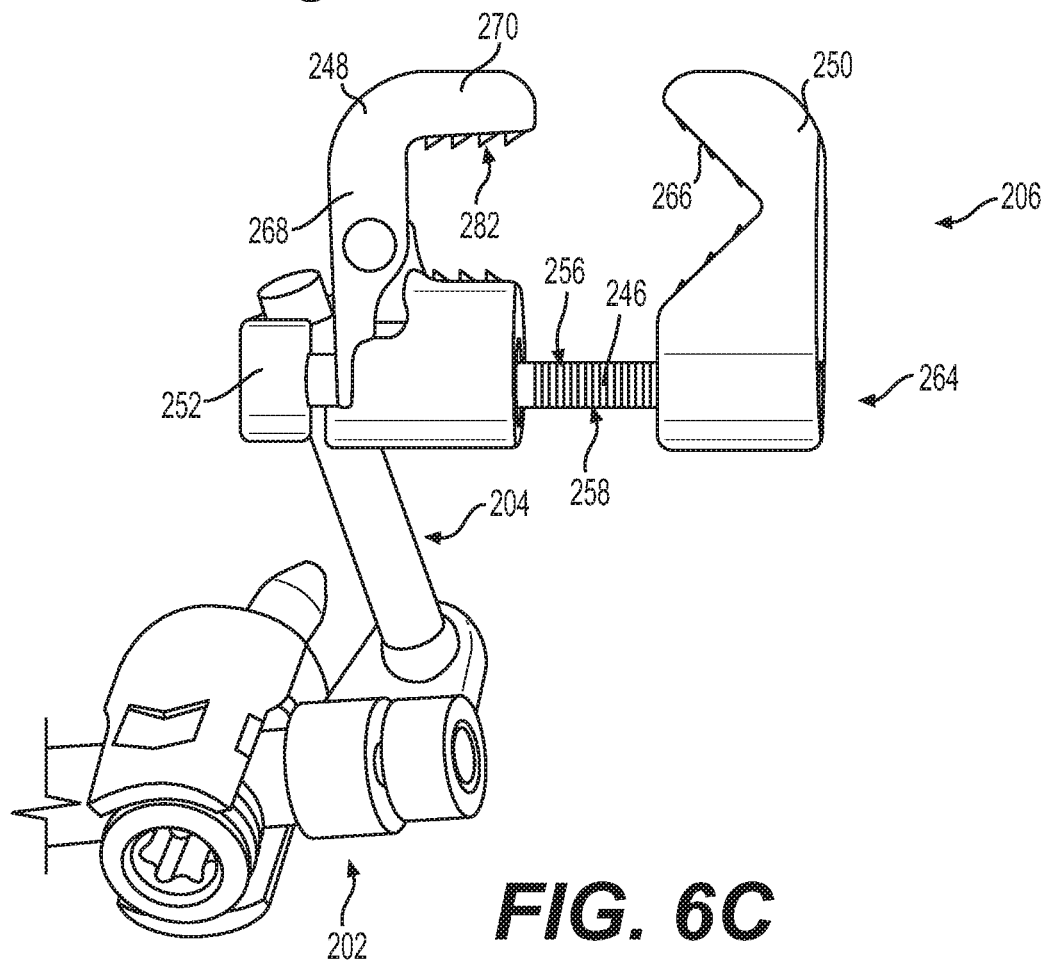

As illustrated in FIGS. 6E-F, the clamp rod 246 can include a head 304 at one end, a tip 312 at another end, and a cylindric (e.g., partially cylindrical) section 254 therebetween. The head 304 can include a socket therein. The socket can include a retaining feature, such as internal threading or a cam groove. In some embodiments, the socket can also be configured to receive a tool, such as a hex key or other driver. The tip 312 can be tapered. In some embodiments, it can be frustoconical. In some embodiments, both the head 304 and the tip 312 may have a non-threaded exterior surface. As illustrated in FIG. 6C, the cylindric section 254 can include two parallel flat surfaces 256, 258. The cylindric section 254 can also include two curved surfaces 260, 262, as illustrated in FIG. 6E-F. In some embodiments, the curved surfaces 260, 262 can each include a plurality of ratcheting receivers, valleys, grooves, and/or other surface features including a series of depressions. In some embodiments, the forward and backward slopes of each depression may be non-symmetrical and/or angled, so as to promote movement in one direction and inhibit movement in another, opposite direction.

As illustrated in FIGS. 6E-F, an extension member 302 may be coupled with the clamp rod 246. The extension member 302 can include a first end 306 and a second end 308. In some embodiments, both the first end 306 and the second end 308 can be cylindrical. As illustrated in FIG. 6E-F, the second end 308 can have a diameter that is greater than that of the first end 306. The first end 306 of the extension member 302 can be configured to be received within the socket of the clamp rod 246. The first end 306 can include a retaining feature, such as external threading or a cam lock, which is configured to mate or engage with the retaining feature of the socket of the clamp rod 246. The second end 308 of the extension member 302 can include a socket therein. In some embodiments, the socket of the second end 308 may be configured to receive a tool, such as a hex key or other driver, therein. The socket may be also be configured to receive the second securing element 274 therein, as illustrated in FIGS. 6E-F. In some embodiments, the socket can optionally include a retaining feature, such as internal threading or a cam groove.

The second translating jaw 250 may be configured to translate linearly along the clamp rod 246. As illustrated in FIG. 6C, the second translating jaw 250 can include an inner surface defining a bore 264 configured to receive the clamp rod 246 therethrough. The inner surface can include at least one ratcheting protuberance extending into the bore 264 and that can be configured to mate and/or engage with the ratcheting receivers of the clamp rod 246. In some embodiments, the inner surface can include two ratcheting protuberances that each align with one of the curved surfaces 260, 262. When mounted on the clamp rod 246, the second translating jaw 250 may be configured to transition between a first, unlocked configuration and a second, locked configuration. In the first, unlocked configuration, the ratcheting protuberances of the translating jaw 250 may be aligned with the flat surfaces 256, 258 of the clamp rod 246. In this configuration, the translating jaw 250 may be able to translate along a length of the clamp rod 246. The translating jaw 250 may transition to the second, locked configuration by being rotated about the clamp rod 246 by approximately 90 degrees. When rotated, the ratcheting protuberances may engage the ratcheting receivers on the curved surfaces 260, 262 of the clamp rod 246, thereby locking the lateral position of the second translating jaw 250 with respect to the clamp rod 246. As illustrated in FIG. 6C, the second translating jaw 250 may include a medial surface 266 that may be configured to contact a bone structure, such as a spinous process. As illustrated in FIG. 6C, the medial surface 266 can be shaped to maximize contact with the bone structure. In some embodiments, the medial surface 266 can be V-shaped, U-shaped, square, or rectangular. The medial surface 266 can also include one or more surface projections, such as teeth, spikes, studs, fins, and/or barbs that can increase friction between the medial surface 266 and the bone structure.

As illustrated in FIG. 6C, the first articulating jaw 248 can include a first section 268 and a second section 270. The first and second sections 268 and 270 may be oriented at an approximately 90 degree angle (e.g., generally perpendicular) relative to one another to form an L shape, and may form a monolithic, unitary body. In other embodiments, the first and second sections 268, 270 may be formed separately and bonded together, e.g., via welding. The first section 268 may include a first, proximal end 280 having a through bore 272, as illustrated in FIG. 6E-F. The through bore 272 may be configured to receive the clamp rod 246 and/or a second securing element 274 therein. In some embodiments where the second securing element 274 includes a set screw having external threading, the through bore 272 may also include internal threading to mate with the second securing element 274. In other embodiments, the proximal end 280 of the first articulating jaw 248 may be slideably disposed on or over the clamp rod 246 and/or the second securing element 274.

The first articulating jaw 248 may be coupled to the second locking member 252 in a way that allows the first articulating jaw 248 to pivot, rotate, and/or articulate relative to the second locking member 252. For example, in some embodiments, the first articulating jaw 248 may be hingedly coupled to the second locking member 252. In these embodiments, the first articulating jaw 248 may include a receptacle 276 (e.g., a through bore or depression) for receiving a shaft 278 of the second locking member 252 therein, as illustrated in FIGS. 6E-F. Optionally, the first articulating jaw 248 may also include a cut-out section 284, as illustrated in FIG. 6D. As illustrated in FIG. 6D, a portion of the second locking member 252 adjacent to the shaft 278 may be inset, nested, or received within the cut-out section 284. As described further herein, those skilled in the art may appreciate that the first articulating jaw 248 can be configured to rotate about the shaft 278 of the second locking member 252. Accordingly, the first articulating jaw 248 may be configured to pivot between an open configuration, as illustrated in FIG. 6E, and a closed configuration, as illustrated in FIG. 6F. Additionally, the receptacle 276 can include a longitudinal axis that is orthogonal to a longitudinal axis of the through bore 272. Thus, when the first articulating jaw 248 pivots about the shaft 278, the proximal end 280 may also be configured to translate linearly relative to the second locking member 252 and/or clamp rod 246.

The second section 270 of the first articulating jaw 248 may be generally elongate. As illustrated in FIG. 6C, the second section 270 may include a medial surface 282 that may be configured to contact a bone structure, such as a spinous process. As illustrated in FIG. 6C, the medial surface 282, alone or in combination with a medial surface of the first section 268 and/or the second locking member 252, can be shaped to maximize contact with the bone structure. In some embodiments, the bone-engaging surface (e.g., the medial surface of the first articulating jaw 248 and the second locking member 252) can be V-shaped, U-shaped, square, or rectangular. At least a portion of the bone-engaging surface, such as medial surface 282, can include one or more surface projections, such as teeth, spikes, studs, fins, and/or barbs that can increase friction between the first articulating jaw 248 and the bone structure.

As illustrated in FIG. 6D-F, the second locking member 252 can include a first, outer ring 286, a second, inner ring 288, and a collar 290. The collar 290 can adjoin or connect the first and second rings 286, 288. The first and second rings 286, 288 can be separated by a gap 294, as illustrated in FIGS. 6E-F. The collar 290 may have a rounded, partially rounded, spherical, partially spherical, spheroidal, or partially spheroidal inner surface defining a conduit 292. The conduit 292 may extend through the collar 290 and can be configured to receive a portion of the translateral support member 204, such as the second enlarged member 244. The conduit 292 can be in fluid communication with the gap 294. The second locking member 252 can also include a bore 296, as illustrated in FIG. 6D. At least a section of the bore 296 can include internal threading. The bore 296 can pass through at least a portion of the first and/or second rings 286, 288, and can share a longitudinal axis with that of the clamp rod 246. In some embodiments, the bore 296 may pass completely though the first ring 286. In other embodiments, the bore 296 may pass completely through the second ring 288. In yet other embodiments, the bore 296 may be internally-threaded in the first ring 286 and not threaded in the second ring 288. The bone screw assembly 202 can also include an externally-threaded second securing element 274, which may be configured to be received within the bore 296 of the second locking member 252. In some embodiments, at least a portion of the second securing element 274, the clamp rod 246, and the extension member 302 may be disposed in the portion of the bore 296 within the second ring 288.

As illustrated in FIG. 6E, the second ring 288 of the second locking member 252 can include a rod-coupling portion 289 and an arm 300 extending generally perpendicularly therefrom. The arm 300 can include shaft 278 extending perpendicularly therefrom. As described herein, the shaft 278 of the second locking member 252 may be received within the receptacle 276 of the first articulating jaw 248 to create a hinge. The rod-coupling portion 289 can include a generally cylindrical outer surface. As described herein, the bore 296 can pass through the rod-coupling portion 289. The rod-coupling portion 289 may be configured to receive at least a portion of the second securing element 274, extension member 302, first articulating jaw 248, and/or clamp rod 246 therein. In some embodiments, the rod-coupling portion 289 may be immovably disposed (e.g., not configured to translate or slide linearly) relative to the clamp rod 246. In other embodiments, the rod-coupling portion 289 may be configured to translate or slide linearly relative to the clamp rod 246. In some embodiments, the rod-coupling portion 289 may be threaded onto, or otherwise in direct engagement with, the clamp rod 246 and/or extension member 302, described herein. In other embodiments, the rod-coupling portion 289 may be indirectly coupled or engaged with the clamp rod 246 and/or extension member 302.

The second ring 288 can also include a bone-engaging portion 298 that can extend from the rod-coupling portion 289. The bone-engaging portion 298 can include a medial surface 310 which can be configured to contact a bone structure, such as a spinous process. As described herein, the medial surface 310, alone or in combination with the medial surface of the first articulating jaw 248, can be shaped to maximize contact with the bone structure. At least a portion of the medial surface 310 can include one or more surface projections, such as teeth, spikes, studs, fins, and/or barbs that can increase friction between the second locking member 252 and the bone structure.

As illustrated in FIGS. 6E-F, the first articulating jaw 248 may be coupled with the second locking member 252 and clamp rod 246 as follows: The extension member 302 may be coupled with the clamp rod 246. The first end 306 of the extension member 302 can be inserted into and engaged with the socket of the clamp rod 246. The extension member 302 and the clamp rod 246 can be positioned in the bore 296 within the second ring 288 of the second locking member 252. As illustrated in FIGS. 6E-F, the first articulating jaw 248 can be positioned within the gap 294 of the second locking member 252 such that the through bore 272 of the first articulating jaw 248 aligns with the bore 296 of the second locking member 252. Additionally, the shaft 278 of the second locking member 252 may be received within the receptacle 276 of the first articulating jaw. The second securing element 274 can then pass through (e.g., engage or thread into) the first ring 286 and the first articulating jaw 248, thereby coupling the first articulating jaw 248 to the second locking member 252.

Figure 7A:
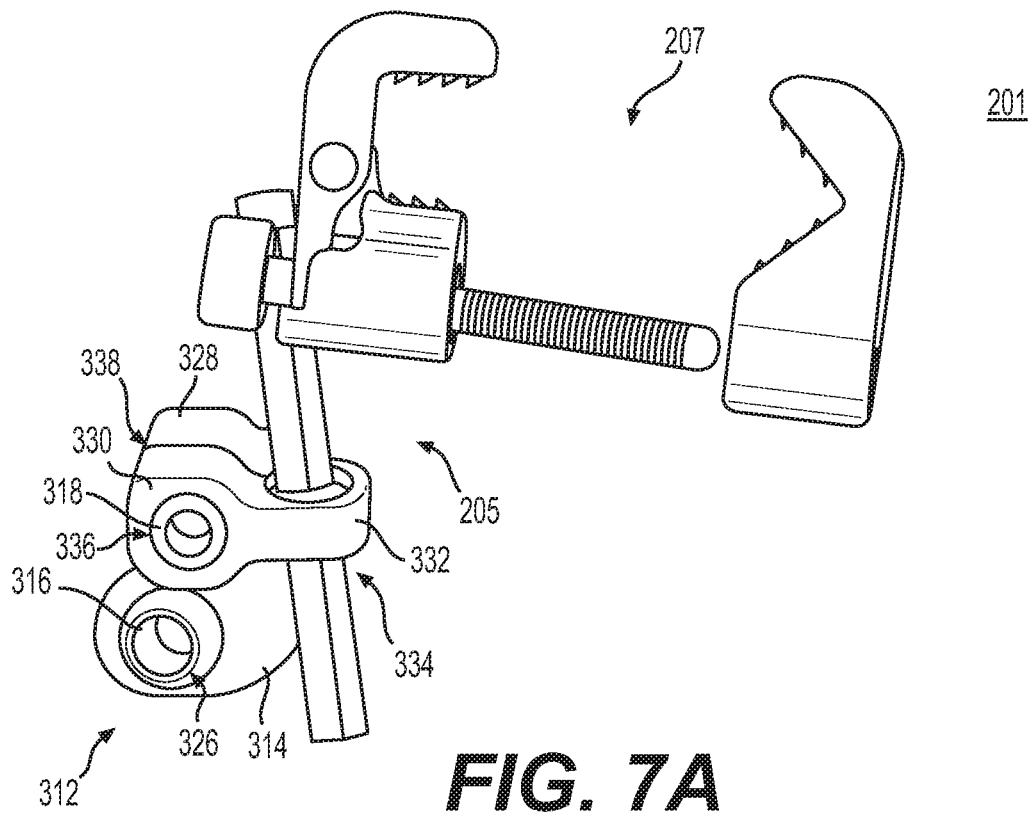
FIGS. 7A-C illustrate one embodiment of a spinal implant assembly that includes a plate assembly.
Figure 7B:
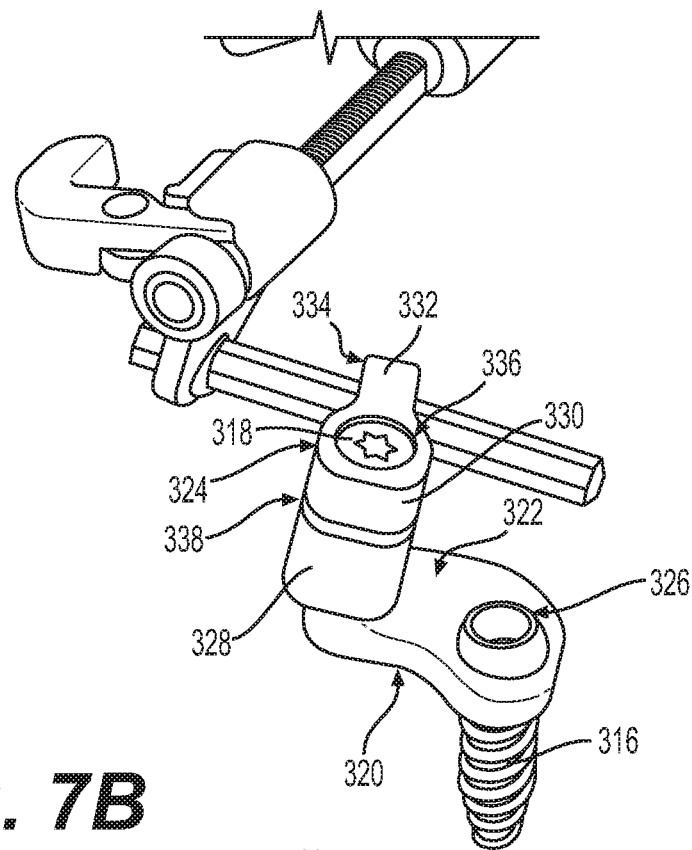
Figure 7C:
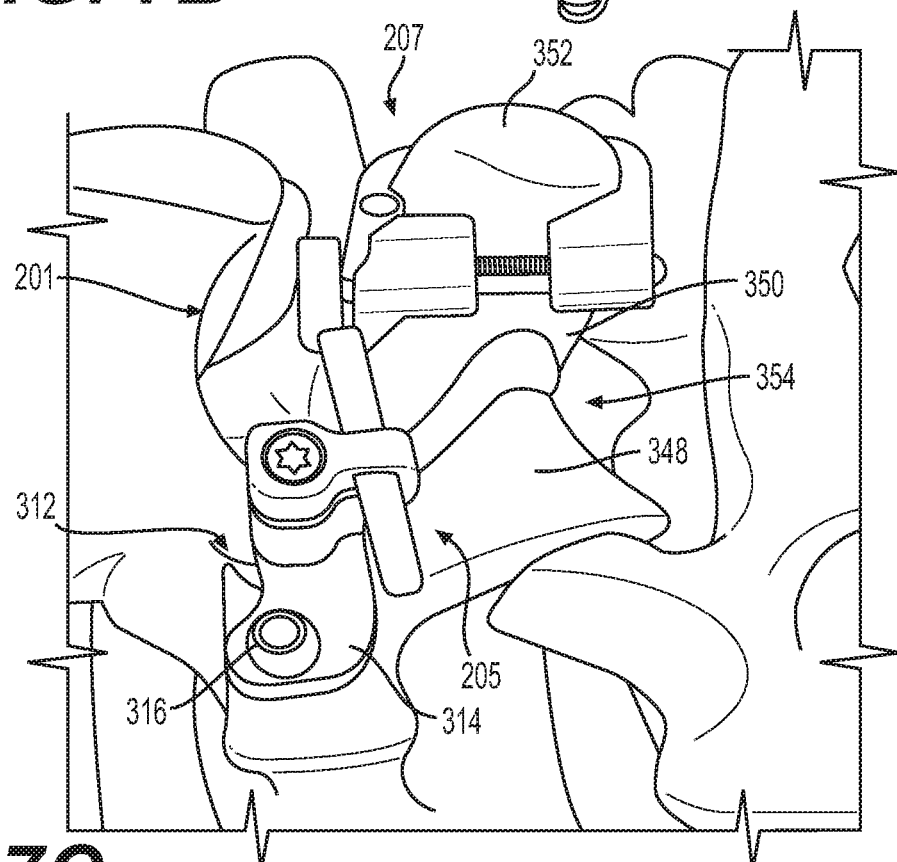

One example of a spinal implant assembly 201 having an alternative anchor member is illustrated in FIG. 7A-C. In these embodiments, the anchor member can include a plate assembly 312. As illustrated in FIG. 7A, the spinal implant assembly 201 can also include a translateral support member 205 and a clamp member 207, which can have some or all of the same features as the translateral support member 204 and clamp member 206 discussed herein. The plate assembly 312 can include a plate member 314. A fastener member 316 and/or a first securing element 318 can also be included with the plate assembly 312. In other embodiments, they may be provided separately. The fastener member 316 can include a head and an elongate, threaded body. In some embodiments, the fastener member 316 can be a bone screw, such as a pedicle screw. The first securing element 318 can include an externally-threaded portion. In some embodiments, the first securing element 318 may be a set screw. As illustrated in FIG. 7B, the plate member 314 can include a lower surface 320 and an upper surface 322. In some embodiments, the lower surface 320 can be generally flat, planar, and/or smooth. The upper surface 322 can include a first locking member 324. The first locking member 324 can be configured to receive at least a portion of the translateral support member 205 therethrough. The plate member 314 can also include a hole 326 passing through from the lower surface 320 to the upper surface 322. As illustrated in FIGS. 7A-B, the hole 326 can be configured to receive the body of the fastener member 316 therethrough. The hole 326 may have a diameter that is greater than that of the body of the fastener member 316 and less than that of the head of the fastener member 316.

As illustrated in FIGS. 7A-B, the first locking member 324 can include a first, inner ring 328, a second, outer ring, 330, and a collar 332 adjoining or connecting the first and second rings 328, 330. The first and second rings 328, 330 can be separated by a gap 338. The collar 332 may have a rounded, partially rounded, spherical, partially spherical, spheroidal, or partially spheroidal inner surface defining a conduit 334. The conduit 334 may extend through the collar 332 and may be configured to receive a portion of the translateral support member 205, such as a first enlarged member, therein. The conduit 334 may be in fluid communication with the gap 338. The first locking member 324 can also include an internally-threaded bore 336, which can pass at least partially through the first and/or second rings 328, 330. The bore 336 can have a longitudinal axis that is orthogonal to a longitudinal axis of the conduit 334. The longitudinal axis of the bore 336 can also be parallel to a longitudinal axis of the hole 326. The bore 336 can be configured to receive and/or mate with the externally-threaded first securing element 318. In some embodiments, the plate member 314 can be a unitary, monolithic body. In other embodiments, the first locking member 324 can be attached (e.g., welded) to the upper surface 322 of the plate member 314.

Some embodiments herein are directed to methods of installing the spinal implant assembly 200, wherein the anchor member includes bone screw assembly 202. These methods can include providing the spinal implant assembly 200 in an unassembled, partially assembled, or fully assembled state. In embodiments where the spinal implant assembly 200 is partially or fully assembled, some or all of the components of the assembly 200 may be coupled or connected, but some or all of the components may still be capable of rotating, pivoting, and/or translating relative to one another.

Some embodiments can include providing the spinal implant assembly 200 in a partially assembled state. In these embodiments, the rod 222 can be pivotably coupled to the translateral support member 204. For example, the first enlarged member 242 of the translateral support member 204 may be disposed within the collar 230, and the first securing element 238 may be loosely engaged with (e.g., threaded in) the first locking member 224. The first enlarged member 242 may be coupled to, but still configured to pivot within, the collar 230. Similarly, the translateral support member 204 can be pivotably coupled to the first half of the clamp member 206. For example, the second enlarged member 244 of the translateral support member 204 may be disposed within the collar 290, and the second securing element 274 may be loosely engaged with (e.g., threaded in) the second locking member 252. The second enlarged member 244 may be coupled to, but still configured to pivot within, the collar 290. The second half of the clamp member 206 may or may not be coupled with the first half of the clamp member 206. The housing 210 may or may not be coupled with the fastener member 208 of the bone screw assembly 202. For example, in embodiments where the housing 210 is configured for top loading, the fastener member 208 may be coupled with the housing 210 prior to installation.

Figure 6G:
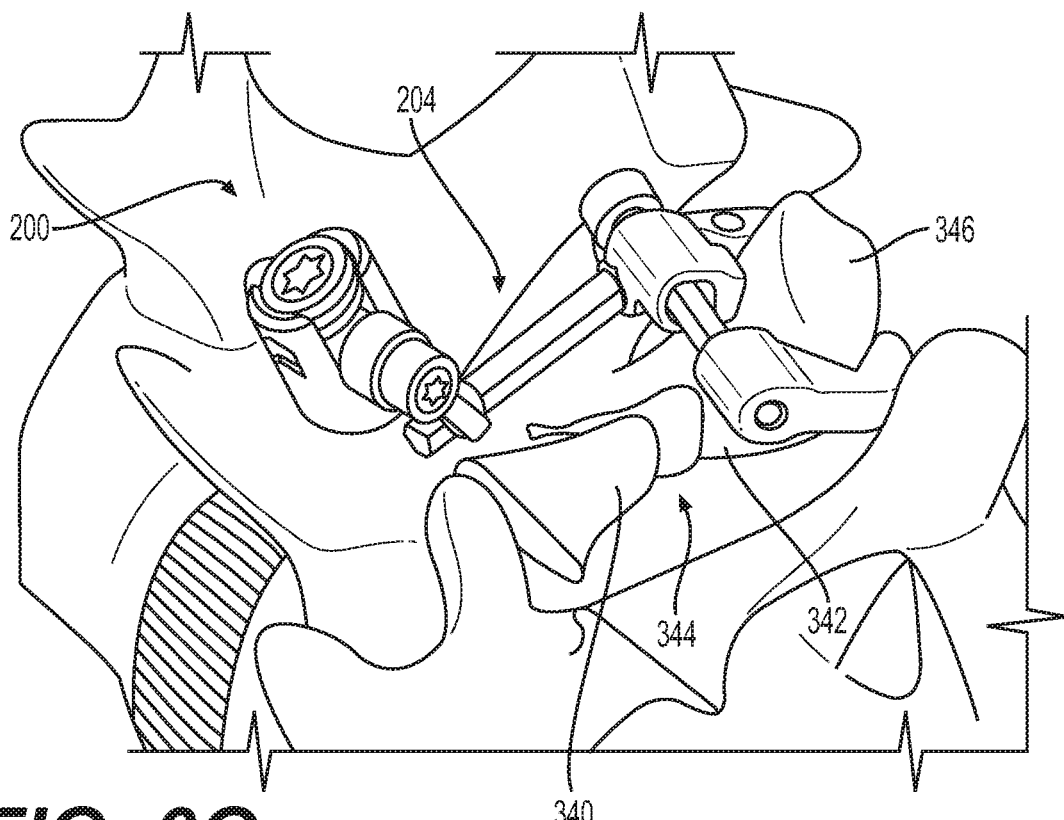

The method can include the step of coupling the anchor member (e.g., bone screw assembly 202) with a bone structure, such as first bone structure 340, described herein. In some embodiments, the spinal implant assembly 200 can be used in conjunction with a laminoplasty procedure. The laminoplasty can be performed in accordance with standard techniques known to those of skill in the art. As illustrated in FIG. 6G, a lamina (e.g., a left lamina) can be completely cut, resulting in first and second bone structures 340, 342. Another lamina (e.g., a right lamina) of the same vertebra can be scored or partially cut to create a hinge. The posterior section of the vertebra may pivot outwards via the hinge, enlarging the spinal canal and creating a gap 344 between the first and second bone structures, 340, 342. As described further herein, the spinal implant assembly 200 can be configured to maintain and/or stabilize the orientation of the first and second bone structures.

The step of coupling the bone screw assembly 202 with first bone structure 340 can include inserting the fastener member 208 into a portion of the first bone structure 340, such as a pedicle. Any techniques known in the art may be used to insert the fastener member 208 into the first bone structure 340. For example, a hole may be drilled in the first bone structure 340 and the fastener member 208 may be threaded into the hole using a driver. In other embodiments, the fastener member 208 may be threaded directly into the first bone structure 340. If not already assembled, the housing 210 and/or coupling element may then be coupled to the fastener member 208.

The method can also include the step of coupling the clamp member 206 with the second bone structure 342. In embodiments where the translateral support member 204 is pre-coupled to the rod 222 and the first half of the clamp member 206, this step can include positioning this construct such that the rod 222 is disposed within the channel 216 of the bone screw assembly 202, and, threading the set screw 220 into the housing member 210. In some embodiments, the set screw 220 may be loosely threaded into the housing member 210 such that the rod 222 is secured to the housing member 210 but is still configured for rotational motion relative to the housing member 210. Additionally, this construct may be positioned such that the first half of the clamp member 206 is positioned adjacent to the second bone structure 342. As illustrated in FIG. 6G, the first half of the clamp member 206 may be positioned near or against a superior surface of a spinous process 346. Additionally, those skilled in the art may recognize that the translateral support member 204 may span the gap 344 between the first bone structure 340 and the second bone structure 342. In other embodiments, one or more of these components (e.g., the rod 222, translateral support member 204, second locking member 252, first articulating jaw 248, and/or clamp rod 246) may be installed separately. Advantageously, the use of clamp member 206 can reduce or prevent damage or trauma to the ligaments surrounding the spinous process 346, as compared to using another anchor such as a pedicle screw. For example, the clamp member 206 may be positioned beneath the supraspinous ligament without needing to cut this ligament. Additionally, if another anchor were installed, e.g., in an opposite pedicle, there could be limited space to position the translateral support member 204 between adjacent spinous processes. Therefore, the clamp member 206 may effectively utilize the space available in the vertebral area.

If not preassembled prior to implantation, the second half of the clamp member 206 (e.g., second translating jaw 250) may then be coupled to the first half of the clamp member 206. As illustrated in FIG. 6G, the second translating jaw 250 may be positioned adjacent to an inferior surface of the spinous process 346. The second translating jaw 250 may be mounted on the clamp rod 246 by sliding the clamp rod 246 through the bore 264. During this step, the ratcheting protuberances extending from the inner surface of the bore 264 may be aligned with the flat surfaces 256, 258 of the clamp rod 246. When the desired lateral position is reached, the second translating jaw 250 may be locked by rotating the clamp rod 246 by approximately 90 degrees. In some embodiments, a tool may be used to apply torque to the clamp rod 246 through the head 304 of the clamp rod 246 or the second end 308 of the extension member 302. As described herein, when the clamp rod 246 is rotated approximately 90 degrees, the ratcheting protuberances on the second translating jaw 250 may engage the ratcheting receivers on the curved surfaces 260, 262 of the clamp rod 246, thereby locking the lateral position of the second translating jaw 250 with respect to the clamp rod 246.

The method can also include the step of locking the spinal implant assembly 200, so that the various members are at a fixed orientation (e.g., unable to rotate or pivot) relative to each other. This step can include locking the set screw 220, the first locking member 224, and/or the second locking member 252. When the set screw 220 is threaded into the housing member 210, the set screw 220 may exert pressure on the rod 222 and fastener member 208, thereby locking the angle of the fastener member 208 relative to the housing member 210 and rod 222. When the first securing element 238 is threaded into the bore 236, the first and second rings 226, 228 may be brought together, closing the gap 234 and causing the collar 230 to constrict around the first enlarged member 242, thereby locking the angle of the translateral support member 204 relative to the pedicle screw assembly 202. The second securing element 274 may be threaded into the bore 296 of the second locking member 252 and further into the bore 272 of the first articulating jaw 248. In use, the action of threading the second securing element 274 into the bore 272 may cause the first articulating jaw 248 to pivot, with the second section 270 pivoting towards the bone engaging portion 298 of the second locking member 252, thereby causing the first articulating jaw 248 to transition from an open configuration (illustrated in FIG. 6E) to a closed configuration (illustrated in FIG. 6F). Additionally, this action may also cause the first and second rings 286, 288 to be pulled together, closing the gap 294 and causing the collar 290 to constrict around the second enlarged member 244, thereby locking the angle of the translateral support member 204 relative to the clamp assembly 206.

Those skilled in the art may appreciate that, prior to locking the spinal implant assembly 200, the assembly 200 can include three variable angle joints (e.g., between the fastener 208 and the rod 222, between the rod 222 and the translateral support member 204, and between the translateral support member 204 and the clamp member 206). Additionally, the rod 222 may also be configured for rotational motion. Advantageously, the variable angle joints and/or rotatable rod can provide flexibility and easier adjustment during placement of the various components of the spinal implant assembly 200, as compared to a similar assembly that may lack these features. Once in the locked configuration, the spinal implant assembly 200 may be configured to maintain the orientation of the first and second bone structures 340, 342, including the gap 344, as established during the laminoplasty.

Other embodiments herein are directed to methods of installing the spinal implant assembly 201, wherein the anchor member includes plate assembly 312. These methods can include providing the spinal implant assembly 201 in an unassembled, partially assembled, or fully assembled state. In embodiments where the spinal implant assembly 201 is partially or fully assembled, some or all of the components of the assembly 201 may be coupled or connected, but some or all of the components may still be capable of rotating, pivoting, and/or translating relative to one another.

Some embodiments can include providing the spinal implant assembly 201 in a partially assembled state. In these embodiments, the translateral support member 205 can be pivotably coupled to the first half of the clamp member 207, as discussed herein with respect to the spinal implant assembly 200. The first securing element 318 may be loosely engaged with (e.g., threaded into) the bore 336 of the first locking member 324. In some embodiments, the translateral support member 205 may also be pivotably coupled to the plate member 314. For example, a first enlarged member may be coupled to, but still configured to pivot within, the collar 332, as discussed herein with respect to the spinal implant assembly 200.

The method can include the step of coupling the anchor member (e.g., plate assembly 312) with a bone structure, such as a first bone structure 348, illustrated in FIG. 7C. The first bone structure 348 can include the same qualities as the first bone structure 340. Additionally, it is noted that the spinal implant assembly 201 can be used in conjunction with a laminoplasty procedure as discussed with respect to spinal implant assembly 200. The step of coupling the plate assembly 312 with the first bone structure 348 can include inserting the fastener member 316 through the hole 326 and into a portion of the first bone structure 348, such as a pedicle. Advantageously, the plate assembly 312 may have a relatively low profile compared to other types of anchors. Any techniques known in the art may be used to insert the fastener member 316 into the first bone structure 348. For example, a hole may be drilled in the first bone structure 348 and the fastener member 316 may be threaded into the hole using a driver. In other embodiments, the fastener member 316 may be threaded directly into the first bone structure 348. Advantageously, the plate member 314 may be loosely coupled to the first bone structure 348 so that it may pivot about the fastener member 316.

The method can also include the step of coupling the clamp member 207 with a second bone structure 350, as illustrated in FIG. 7C. In embodiments where the translateral support member 205 and the plate member 314 are not pre-coupled prior to installation, this step can include first include coupling the translateral support member 205 with the plate member 314 as discussed herein. The first half of the clamp member 207 may also be positioned adjacent to the second bone structure 350, e.g., near or against a superior surface of a spinous process 352. Additionally, those skilled in the art may recognize that the translateral support member 205 may span the gap 354 between the first bone structure 348 and the second bone structure 350. In other embodiments, one or more components (e.g., clamp member 207 components) may be installed separately, as discussed with respect to spinal implant assembly 200. If not preassembled prior to implantation, the second half of the clamp member 207 may be coupled to the first half of the clamp member 207, as discussed with respect to spinal implant assembly 200.

The method can also include the step of locking the spinal implant assembly 201, so that the various members are at a fixed orientation (e.g., unable to rotate or pivot) relative to each other. This step can include locking the plate member 314, the first locking member 324, and/or a second locking member (possessing the same qualities as second locking member 252) disposed in the clamp member 207. The fastener member 316 can be firmly threaded into the first bone structure 348 so as to lock the plate member 314 to the first bone structure 348 at a particular orientation. The first and second locking members of the spinal implant assembly 201 can be locked as discussed herein with respect to first and second locking members 224, 252.

Those skilled in the art may appreciate that, prior to locking the spinal implant assembly 201, the assembly 201 can include two variable angle joints (e.g., between the plate assembly 312 and the translateral support member 205, and between the translateral support member 205 and the clamp member 207). Additionally, the plate member 314 may be configured to pivot about the fastener member 316. Advantageously, the variable angle joints and/or pivotable plate can provide flexibility and easier adjustment during placement of the various components of the spinal implant assembly 201, as compared to a similar assembly that may lack these features. Once in the locked configuration, the spinal implant assembly 201 may be configured to maintain the orientation of the first and second bone structures 348, 350, including the gap 354, as established during the laminoplasty.

In some instances, a laminectomy may be performed to relieve pressure on spinal nerves and/or expand a spinal canal. In these procedures, the laminae and spinous process may be completely removed. Some embodiments herein are directed to spinal implant assemblies that can stabilize a spine in the absence of these spinal structures. Some embodiments can preserve, maintain, or enable the vertebrae to move relative to one another. Advantageously, the spinal implant assemblies described herein may have interchangeable components, enabling a practitioner to tailor a particular spinal implant assembly to the needs of an individual. As one example, the various components can be altered to adjust the weight or load placed on the underlying vertebra, so as to promote controlled bone growth.

Turning now to FIGS. 8A-11D, a spinal implant assembly 400 is illustrated in accordance with embodiments described herein. The spinal implant assembly 400 can include a superior (e.g., upper or cephelad) translateral stabilization system 402, an inferior (e.g., lower or caudal) translateral stabilization system 404, and a secondary stabilization system 406. The secondary stabilization system 406 can be configured to couple two adjacent vertebrae. A variety of different systems may be used for the superior and inferior translateral stabilization systems. In some embodiments, the superior and/or inferior translateral stabilization systems can include a facet stabilization device and/or a translateral plate. Similarly, a variety of different systems may be used for the secondary stabilization system. For example, the secondary stabilization system can include an intervertebral member (e.g., an interbody spacer or an artificial disc), one or more members configured to couple the superior and inferior translateral stabilization systems (e.g., a static or dynamic rod), and/or one or more members configured to directly connect the two adjacent vertebrae (e.g., bilateral plates or rods). Those skilled in the art may appreciate that these various components may be used alone or in any combination as appropriate for the particular situation. Additionally, those skilled in the art may appreciate that the inferior translateral stabilization system 404 can have some or all of the same features as the superior translateral stabilization system 402. Therefore, any and all discussion herein with respect to the superior translateral stabilization system 402 may also apply to the inferior translateral stabilization system 404.

Figure 8A:
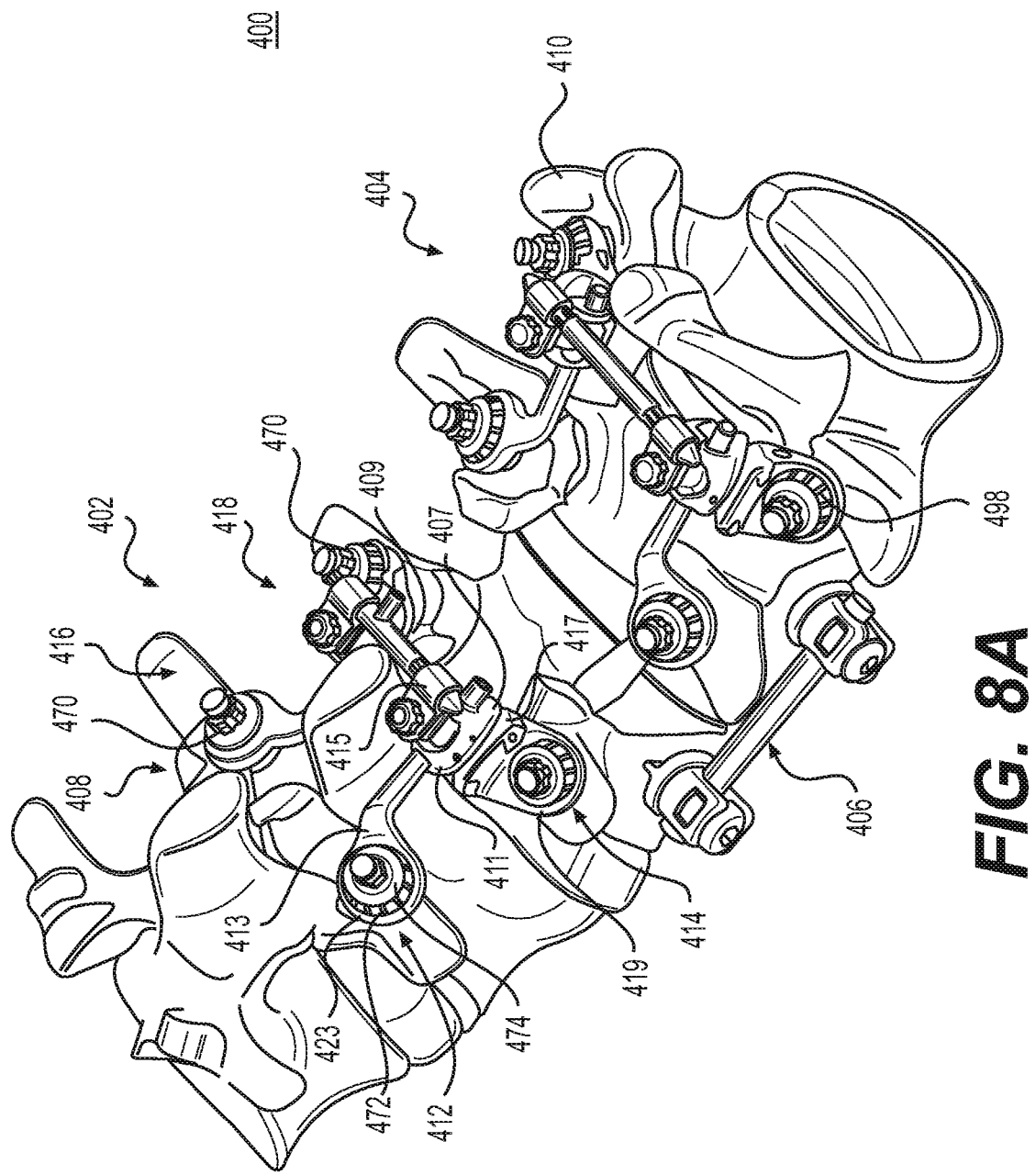
Figure 9:
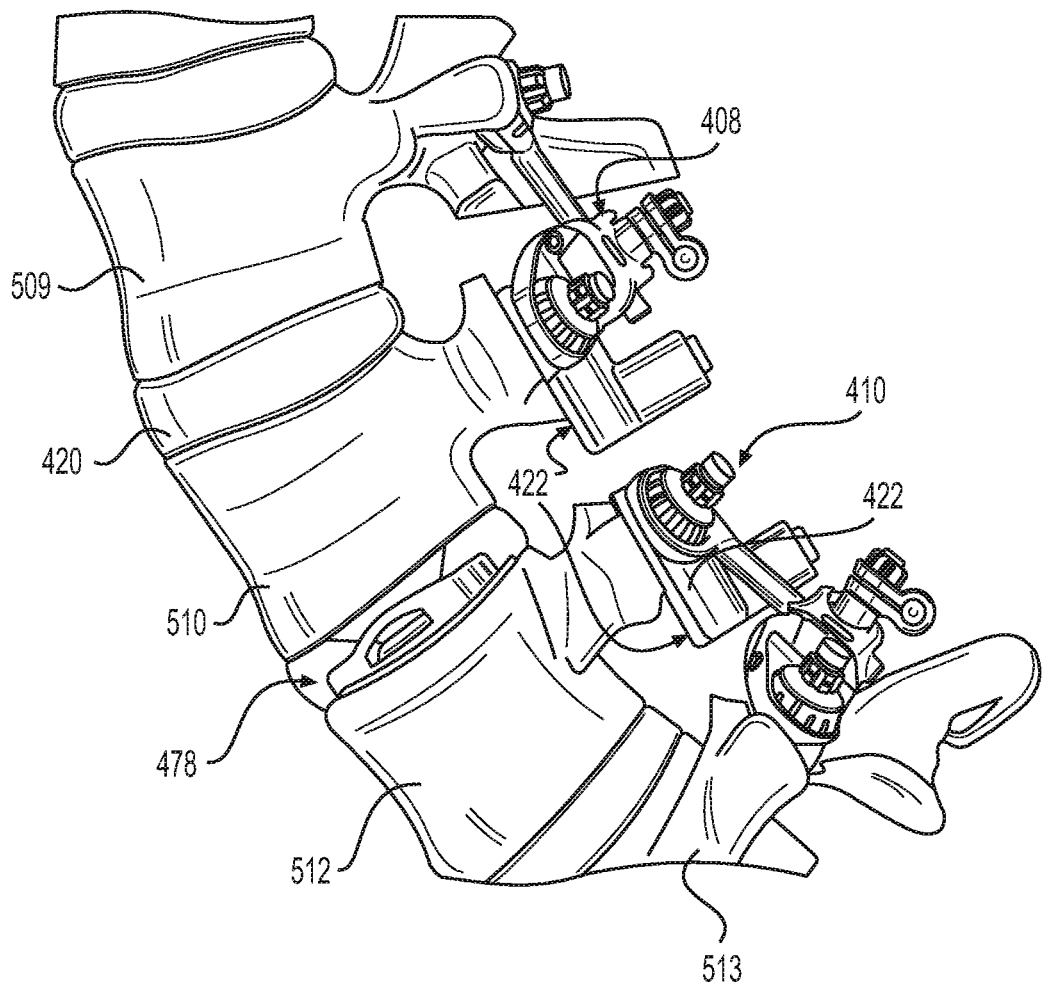
FIG. 9 illustrates one embodiment of an intervertebral member of a spinal implant assembly described herein.

The superior translateral stabilization system can include a first facet stabilization device and/or a first translateral plate. In some embodiments, the superior translateral stabilization system can include both a first facet stabilization device and a first translateral plate, as illustrated in FIG. 9, for example. Turning to FIG. 8A, a perspective view of one embodiment of a spinal implant assembly 400 as implanted in a spine is illustrated. As illustrated, the superior translateral stabilization system 402 can include a first facet stabilization device 408. The inferior translateral stabilization system 404 can include a second facet stabilization device 410. Any facet stabilization devices (e.g., a device configured to replace a natural facet joint or portion thereof) known in the art may be used. For example, in some embodiments, the first facet stabilization device 408 may include a facet joint replacement system as disclosed in U.S. Pat. No. 8,308,768 to Fauth entitled, "System and Method for Facet Joint Replacement," hereby incorporated by reference herein in its entirety.

As illustrated in FIG. 8A, the first facet stabilization device 408 can include a left inferior facet joint prosthesis 412, a left superior facet joint prosthesis 414, a right inferior facet joint prosthesis 416, a right superior facet joint prosthesis 418, and a crosslink rod 409. Each of the facet joint prostheses may be configured to receive a fixation assembly 470 therein. The left inferior facet joint prosthesis 412 can include an inferior articular body 411, an inferior strut 413, and an attachment mechanism 415. The inferior articular body 411 can include an inferior articular surface 407 that is shaped to replace a natural inferior articular surface of a vertebra. The inferior strut 413 can include a ring 423 configured to receive a portion of the fixation assembly 470 therein. The attachment mechanism 415 can be configured to provide polyaxial adjustability between the inferior articular body 411 and the inferior strut 413, and can be configured to receive the crosslink rod 409 therein. The left superior facet joint prosthesis 414 can be monolithic and can include a superior articulation surface 417, a ring 419, and a gripping feature (not shown). The superior articulation surface 417 can be shaped to replace a natural superior articular surface of a vertebra, and can be configured to articulate with the inferior articular surface 407. Those skilled in the art may appreciate that the right inferior and superior facet joint prostheses 416, 418 may include some or all of the same features as the left inferior and superior facet joint prostheses 412, 414, and may be a mirror image of those prostheses.

The fixation assembly 470 can include some or all of the features of the fixation assemblies disclosed in U.S. Pat. No. 8,308,768 to Fauth, incorporated by reference herein. For example, in some embodiments, the fixation assembly 470 can include a fixation member (not shown), such as a pedicle screw, a base member (not shown), a split sphere 472, and a top nut 474. The fixation member can include a distal threaded bone-engaging portion, a shaft, and a proximal threaded attachment portion. The base member can be cannulated throughout, and can include a bone-engaging portion, a flange, and a tapered portion. The tapered portion may include an open end having a tool engagement rim including a plurality of notches. The split sphere 472 may be sized and configured to fit over the tapered portion of the base, and may include a plurality of slits 476 which allow the sphere to be expandable. The top nut 474 can include a threaded bore and a flange which encircles the nut 474. The split sphere 472 may advantageously be configured for polyaxial movement within the rings 413, 419 (or the first hole 464 of the translateral plate 420, discussed herein), or vice versa. Advantageously, during installation, the orientation of the inferior and superior facet joint prostheses 412, 414 may be adjustable after the fixation member(s) have been installed.

Figure 8B:
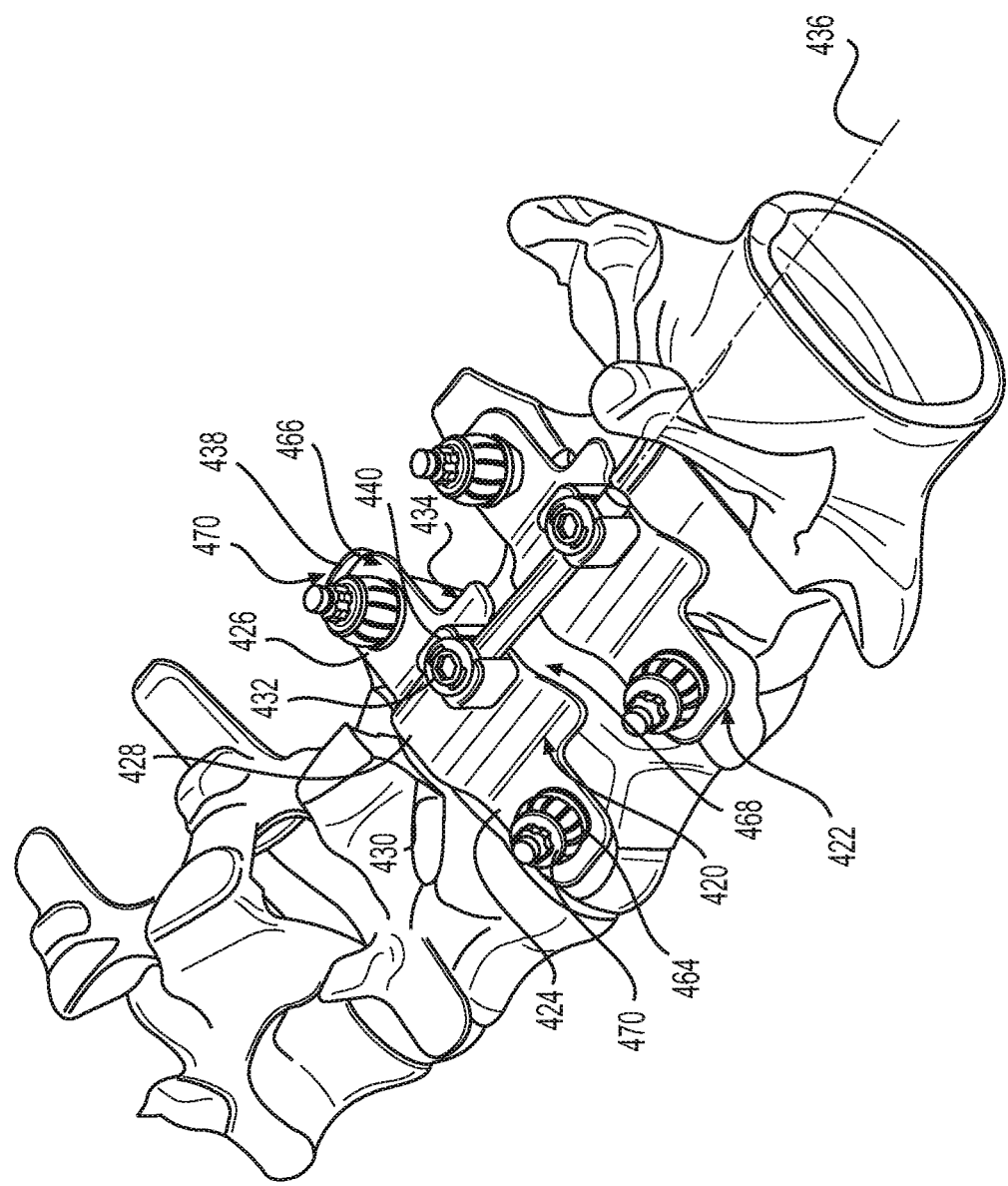

Turning to FIG. 8B, another embodiment of a spinal implant assembly 400 is illustrated. In this embodiment, the superior translateral stabilization system 402 can include a first translateral plate 420. The inferior translateral stabilization system 404 can include a second translateral plate 422. The second translateral plate 422 can include some or all of the features of the first translateral plate 420. The first translateral plate 420 can include a first fixation section 424, a second fixation section 426, and a middle section 428. The shape of the first translateral plate 420 may advantageously be similar to the natural topography of a posterior section of a vertebra. The first translateral plate 420 can have a width as measured along a mediolateral axis and a height as measured along a superior-inferior axis. The width and height of the first translateral plate 420 can be generally equal to the width and the height of a vertebra. In some embodiments, the width of the first translateral plate 420 may generally extend from a left articular process to a right articular process. In other embodiments, the width of the first translateral plate 420 may generally extend from a left transverse process to a right transverse process. The height of the middle section 428 can be greater than the height of the first and/or section fixation sections 424, 426. The heights of the first and/or section fixation sections 424, 426 can be equal. As illustrated in FIG. 8B, for example, the first translateral plate 420 may have a top surface and a bottom surface that are each non-planar (e.g., curved). The middle section 428 may be elevated relative to the first and second fixation sections 424, 426. Consequently, there may be a gap 468 below the middle section 428. Advantageously, in embodiments where the first translateral plate 420 is installed on a vertebra on which a laminectomy has been performed, the first translateral plate 420 can protect the spinal canal while the gap 468 can increase the space available for nerves in the spinal canal.

The first and second fixation sections 424, 426 can be configured to engage first and second bone structures (e.g., left and right pedicles on a vertebra). For example, the first fixation section 424 can include a first hole 464 passing through from a top surface to a bottom surface, and the second fixation section 426 can include a second hole 466 passing through from a top surface to a bottom surface. The first and second holes 464, 466 can be configured to receive a fixation member or assembly, such as a pedicle screw, therein. The middle section 428 can be disposed between and connected to the first and second fixation sections 424, 426. In some embodiments, the first translateral plate 420 can be a unitary body. In other embodiments, the various sections may be connected (e.g., welded) together.

Any fixation member or assembly can be inserted into the first and second holes 464, 466 to secure the first translateral plate 420 to a vertebra. In some embodiments, the fixation member can include a bone screw, such as a pedicle screw. The pedicle screw can be configured for polyaxial or monoaxial motion. In some embodiments, a fixation assembly 470, which can be the same as the fixation assembly described with respect to the first facet stabilization device 408, can be configured to be disposed within the first hole 464 to attach the first fixation section 424 to a first bone structure. A second fixation assembly 470 can also be configured to be disposed within the second hole 466.

In some embodiments, the secondary stabilization system 406 can be configured to couple with the superior and inferior translateral stabilization systems 402, 404. The superior and/or inferior translateral stabilization systems 402, 404 (e.g., first translateral plate 420) can be configured to rigidly or dynamically couple with the secondary stabilization system 406. One example of a rigid connection is illustrated in FIG. 8B. As illustrated in FIG. 8B, the first translateral plate 420 can include a rod-receiving member 430. The rod-receiving member 430 can be disposed on and/or coupled to the middle section 428 of the first translateral plate 420. The rod-receiving member 430 can include a lower portion having a channel 432 and an upper portion having interior threading. The channel 432 can be configured to receive a secondary stabilization system or portion thereof, such as a rod 434, or other secondary stabilization systems described herein. For example, the channel 432 may be U-shaped or may otherwise have a curved lower portion upon which the rod 434 may sit. The rod 434 may be, for example, a solid titanium rod. Additionally, the channel 434 may have a longitudinal axis 436 that is orthogonal to a transverse axis 438 of the first translateral plate 420. The upper portion may be configured to receive a set screw 440.

An example of a superior translateral stabilization system 402 (e.g., first translateral plate 421) configured to dynamically couple with the secondary stabilization system 406 is illustrated in FIG. 8C. The first translateral plate 421 may be similar to the first translateral plate 420, except that it can include a rod-receiving member 431 that is configured to pivot and/or rotate relative to the first translateral plate 421. For example, the rod-receiving member 431 can be connected to the middle section 429 through a ball and socket joint. The rod-receiving member 431 can include a platform 442 having a top surface 444 and a bottom surface 446. The top surface 444 can include two arms 448, 450 extending therefrom and defining a rod-receiving channel 452. The two arms 448, 450 can each include interior threading. As illustrated in FIG. 8D, the bottom surface 446 can include a neck (not shown) that connects the bottom surface 446 to a bottom extension 454. The bottom extension 454 can have a top surface and a partially spherical concave bottom surface or depression. In some embodiments, the bottom surface 446 may not include a neck and/or bottom extension 454. In these embodiments, the bottom surface 446 of the platform 442 may be a partially spherical concave surface.

As illustrated in FIG. 8D, the middle section 429 of the first translateral plate 421 can include a top surface 456 having a partially spherical convex protrusion thereon. The partially spherical convex protrusion and the partially spherical concave depression may have the same radius and/or degree of curvature. In some embodiments, the partially spherical concave protrusion may be configured to nest or be received in the concave depression. Those skilled in the art may appreciate that, upon assembly of the first translateral plate 421, the partially spherical concave bottom surface of the rod-receiving member 431 and the partially spherical convex top surface 456 of the middle section 429 may articulate or pivot with respect to each other, thereby allowing any rod disposed in the rod-receiving member 431 to articulate or pivot as well. Those skilled in the art may appreciate that, in other embodiments, the rod-receiving member 431 may include a convex portion and the middle section 429 of the first translateral plate 421 may include a concave portion. Advantageously, the first translateral plate 421 can allow a vertebra to move or rotate even if it has been coupled to another vertebra.

The first translateral plate 421 can also include first and second side rails 458, 460. The side rails 458, 460 may each extend about the entire height of the middle section 429. The side rails 458, 460 can be attached (e.g., welded) to the upper surface of the middle section 429, and can be disposed on either side of the convex top surface 456. The lower surfaces of the side rails 458, 460 may be concave to match the curvature of the convex top surface 456 and/or the concave bottom surface of the bottom extension 454. As illustrated in FIG. 8D, the side rails 458, 460 may each be attached at two different points on the upper surface of the middle section 429. A window 462 may be created between the attachment points on the side rail 458. Although not illustrated, those skilled in the art may appreciate that a similar window may exist below the second side rail 460. Additionally, as illustrated in FIG. 8D, the side rails 458, 460 may at least partially overlap the bottom extension 454 and the concave top surface 456, such that at least a portion of the bottom extension 454 and the concave top surface 456 are disposed within the window 462 (as well as within the window defined by the second side rail 460). Those skilled in the art may appreciate that the side rails 458, 460 may be configured to maintain engagement between (e.g., prevent separation of) the rod-receiving member 431 and the middle section 429. Additionally, the side rails 458, 460 may be configured to limit the range of articulating, rotational, and/or axial motion of the rod-receiving member 431. For example, in some embodiments, the rod-receiving member 431 may be configured for an axial rotation range of motion of from about 1 degree to about 15 degrees. Those skilled in the art may appreciate that the range of axial rotation can vary on the basis of one or more factors, including but not limited to the dimensions of the side railings and the degree of curvature of the convex and concave surfaces.

As described herein, the spinal implant assembly 400 can include a secondary stabilization system 406. The secondary stabilization system can be configured to couple two adjacent vertebrae. A variety of different systems may be used for the secondary stabilization system. In some embodiments, the secondary stabilization system can include an intervertebral member. The intervertebral member can be configured to fuse two adjacent vertebrae. For example, in some embodiments, the intervertebral member can include a vertebral fusion device, such as an interbody cage. In other embodiments, the intervertebral member can be configured to dynamically couple two adjacent vertebrae. For example, the intervertebral member may be configured to allow relative motion between the two adjacent vertebrae. In one embodiment, the intervertebral member may include an artificial or prosthetic intervertebral disc 478, as illustrated in FIG. 9. Any interbody cages or artificial discs known in the art may be incorporated as part of the secondary stabilization system 406. For example, in some embodiments, the secondary stabilization system 406 can include one or more artificial discs disclosed in U.S. Pat. No. 8,685,103 to Hansell, et al., entitled "Transforaminal Prosthetic Spinal Disc Apparatus," hereby incorporated by reference herein in its entirety.

Figure 10A:
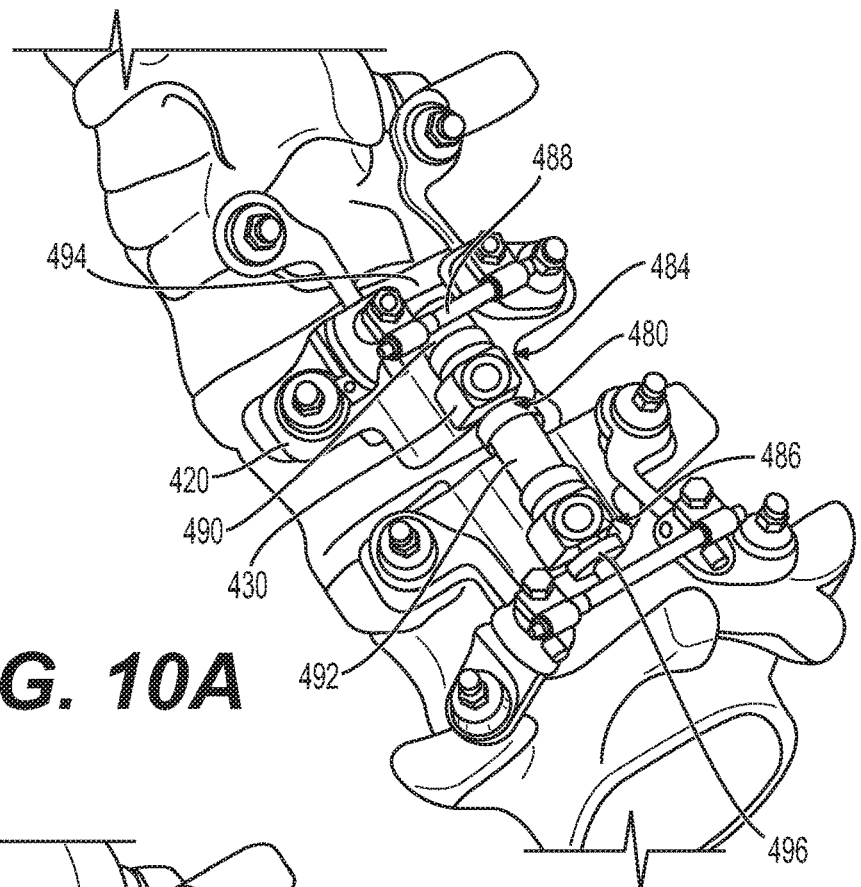
FIGS. 10A-E illustrate embodiments of stabilization system connectors of spinal implant assemblies described herein.
Figure 10B:
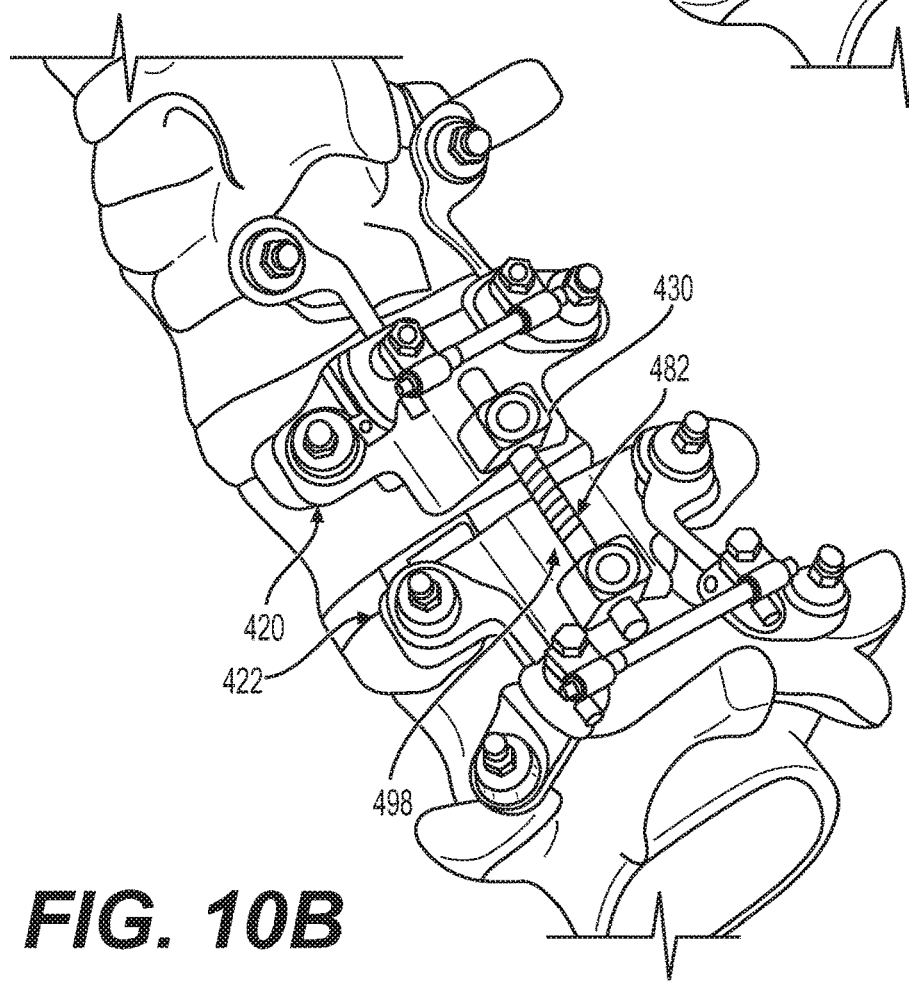

In some embodiments, the secondary stabilization system can be configured to couple with the superior and inferior stabilization systems 402, 404 (e.g., facet stabilization devices 408 and 410, and/or translateral plates 420, 422), in addition to being configured to couple two adjacent vertebrae. In these embodiments, the secondary stabilization system may be referred to as a stabilization system connector. In some embodiments, the secondary stabilization system can be configured to allow or maintain relative motion between the two adjacent vertebrae. For example, the secondary stabilization system can include a dynamic stabilizer 480, as illustrated in FIG. 10A, or a flexible rod 482, as illustrated in FIG. 10B. Any dynamic stabilizers known in the art can be coupled to the first and second translateral plates. For example, the dynamic stabilizer 480 can include one or more elongate connection elements as described in U.S. Pat. No. 8,465,526 to Friedrich et al., entitled "Flexible Spine Stabilization System," and incorporated by reference herein in its entirety. The dynamic stabilizer 480 can include a first attachment portion 484 configured to couple with the first translateral plate 420 or 421 and a second attachment portion 486 configured to couple with the second translateral plate. For example, the first attachment portion 484 can be received within the static rod-receiving member 430, as illustrated in FIG. 10A. In embodiments that include first translateral plate 421, the first attachment portion 484 can be received within the dynamic rod-receiving member 431. The dynamic stabilizer 480 can also include a first end portion 488 and a second end portion 496. A first resilient member 490 can positioned between the first end portion 488 and the first attachment portion 484. A second resilient member 492 can be positioned between the first attachment portion 484 and the second attachment portion 486. These elements can be disposed on a coupling member 494. The first and/or second resilient members 490, 492 can be made from a flexible, soft, and/or elastically resilient or deformable biocompatible material, such as a biocompatible elastomer, silicone, polyurethane or polycarbonate urethane, or any other known similar material.

The flexible rod 482 may be configured to flex, bend, twist, or contort under pressure, e.g., from one or more vertebrae. A variety of features may be used to impart flexibility to the rod 482. As illustrated in FIG. 10B, the flexible rod 482 can include at least one incision, opening, notch, slit, or cut 498. In some embodiments, the flexible rod 482 can include a plurality of cuts. The cut 498 may include one or more linear (e.g., straight), angular, and/or curved sections. The cut 498 may revolve or rotate about a longitudinal axis. For example, the cut 498 can be a helical cut that extends along a length of a body thereof, as illustrated in FIG. FIG. 10B. In embodiments including a cut, the flexible rod 482 may be configured to flex as the result of structural instability that may be generated by the cut 498. Additionally, in these embodiments, the flexible rod 482 can be made from any appropriate biocompatible material, including a metal, such as titanium or alloys thereof, or a polymer, such as PEEK. In other embodiments, a surface of the rod 482 can include at least one groove or trench, instead of or in addition to a cut. In yet other embodiments, the flexible rod 482 may include a flexible, deformable, or malleable material. The flexible rod 482 can be received within the static rod-receiving member 430 of the first translateral plate 420, as illustrated in FIG. 10B. In other embodiments, the flexible rod 482 can be received within the dynamic rod-receiving member 431.

Figure 10C:
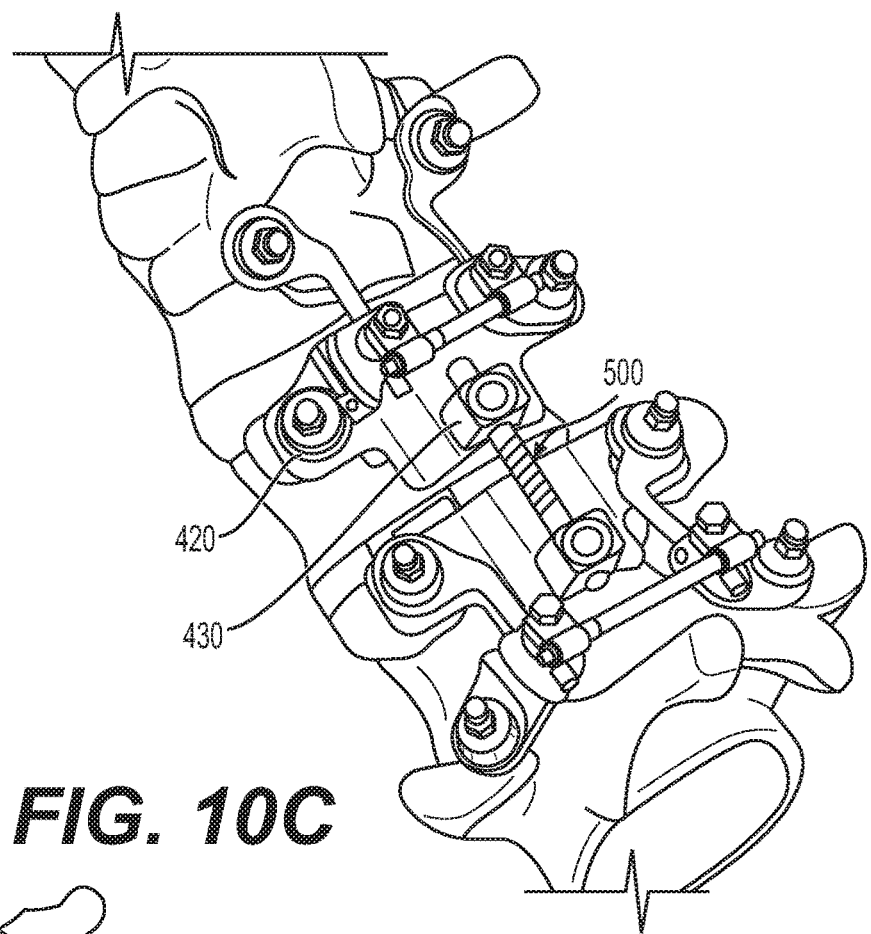
Figure 10D:
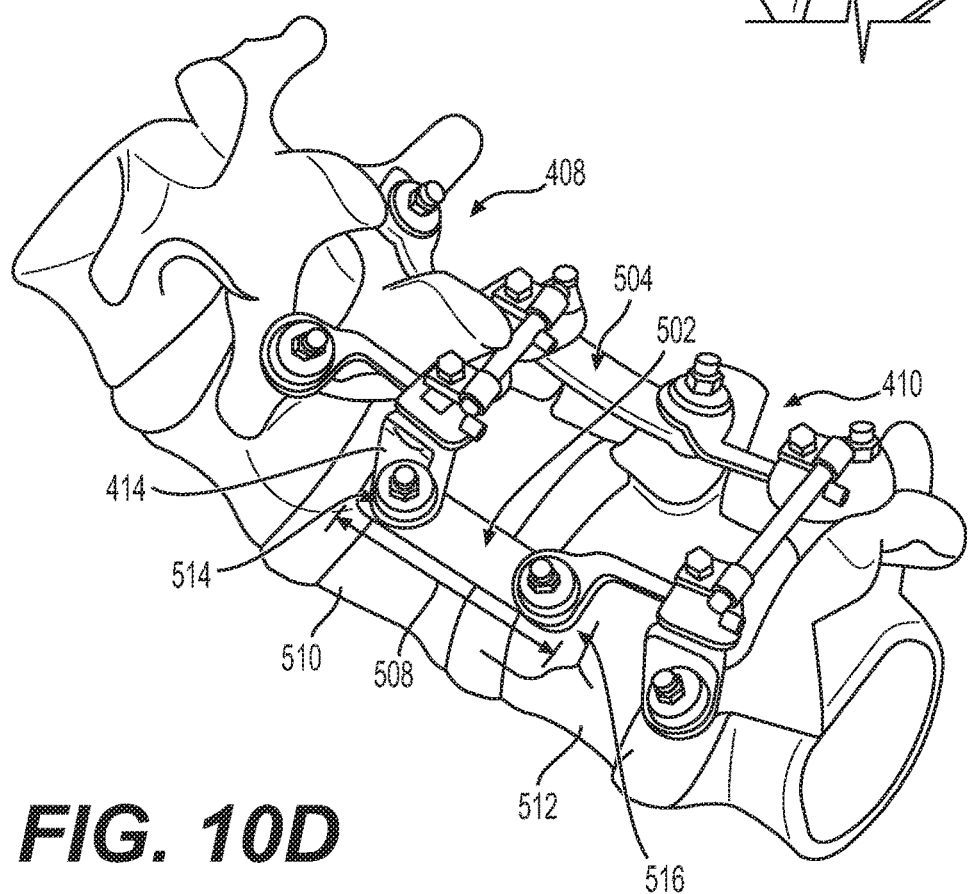
Figure 10E:
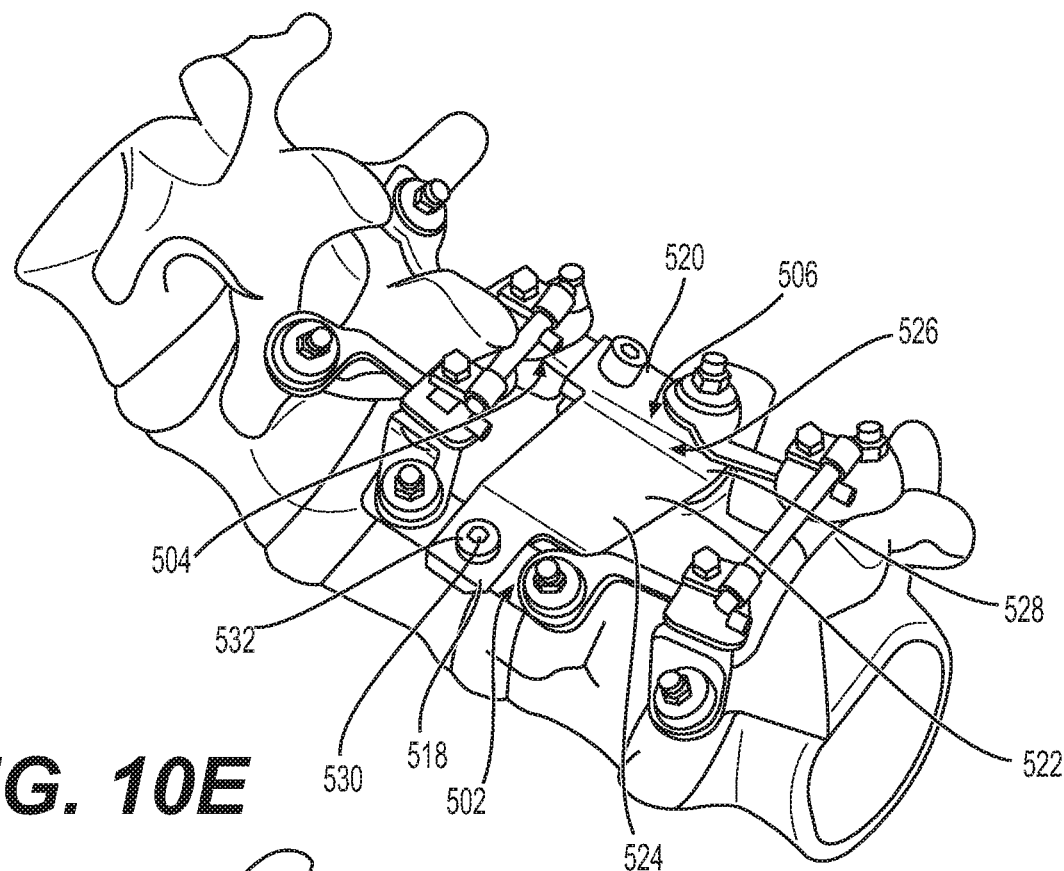

In other embodiments, the secondary stabilization system can be configured to prevent or inhibit relative motion between the two adjacent vertebrae. In these embodiments, the secondary stabilization system can include a rigid rod 500 as illustrated in FIG. 10C, first and second connecting plates 502, 504 as illustrated in FIG. 10D, and/or a prosthetic spinous process 506 as illustrated in FIG. 10E. The rigid rod 500 may be stiff, solid, and/or inflexible. It may be made of any suitable biocompatible material, including a metal, such as titanium or alloys thereof, or a polymer, such as PEEK. The rigid rod 500 may have a circular cross section and can be straight or curved. The rigid rod 500 may have a length configured to span at least from a rod-receiving member on a first translateral plate to a rod-receiving member on a second translateral plate. Similar to the dynamic stabilizer 480 and/or the flexible rod 482, the rigid rod 500 may be configured to be received within the static rod-receiving member 430 of the first translateral plate 420, as illustrated in FIG. 10C. In other embodiments, the flexible rod 482 can be received within the dynamic rod-receiving member 431.

As illustrated in FIG. 10D, the first connecting plate 502 can have a height 508 that can be configured to extend from a superior vertebra 510 to an adjacent, inferior vertebra 512. The first connecting plate 502 can have a generally constant thickness. In some embodiments, the first connecting plate 502 may be flat or planar. In other embodiments, the first connecting plate 502 may be curved, e.g., to match the natural curvature of a spine. The first connecting plate 502 can include a first end having a first hole 514 and a second end having a second hole 516. As illustrated in FIG. 10D, the first hole 514 can be aligned with a portion of the first facet stabilization device 408, such as a ring of the left superior facet joint prosthesis 414. In use, a fixation member can pass through both the ring and the first hole 514, thereby affixing or securing both the first connecting plate 502 and the left superior facet joint prosthesis 414 to the superior vertebra 510. The second hole 516 may be similarly aligned with a portion of the second facet stabilization device 410, such as a left inferior facet joint prosthesis thereof.

As illustrated in FIG. 10E, in some embodiments, the secondary stabilization system can include a prosthetic spinous process 506. The prosthetic spinous process 506 can include a first fixation section 518, a second fixation section 520, and a projection member 522 therebetween. As illustrated in FIG. 10E, the prosthetic spinous process 506 can include a unitary, monolithic body. In other embodiments, the various sections can be joined (e.g., welded) together. The projection member 522 can include a first arm 524 and a second arm 526, each projecting outwards and joining together to form a peak 528. The width of the projection member 522 can taper or be reduced towards the peak 528. In some embodiments, the projection member 522 can have a triangular or V-shaped transverse cross-section.

In some embodiments, the prosthetic spinous process 506 can be configured to couple with the first connecting plate 502, as illustrated in FIG. 10E. In these embodiments, the first fixation section 520 can include a hole for receiving a fastener member 530 therein. In some embodiments, the fastener member 530 can be a screw or bolt. In these embodiments, the first connecting plate 502 may also include a hole in a middle section thereof for receiving the fastener member 530. In other embodiments, the fastener member 530 can include a projection on a surface of the first connecting plate 502. In some embodiments, a nut 532 may be used to mate with the fastener member 530, thereby securing the first fixation section 518 to the first connecting plate 502. The second connecting plate 504 may have some or all of the same features as the first connecting plate 502, and may be configured to couple or adjoin right-side members of the superior and inferior translateral stabilization systems 402, 404 and/or couple with the second fixation section 520 of the prosthetic spinous process 506.

Figure 11A:
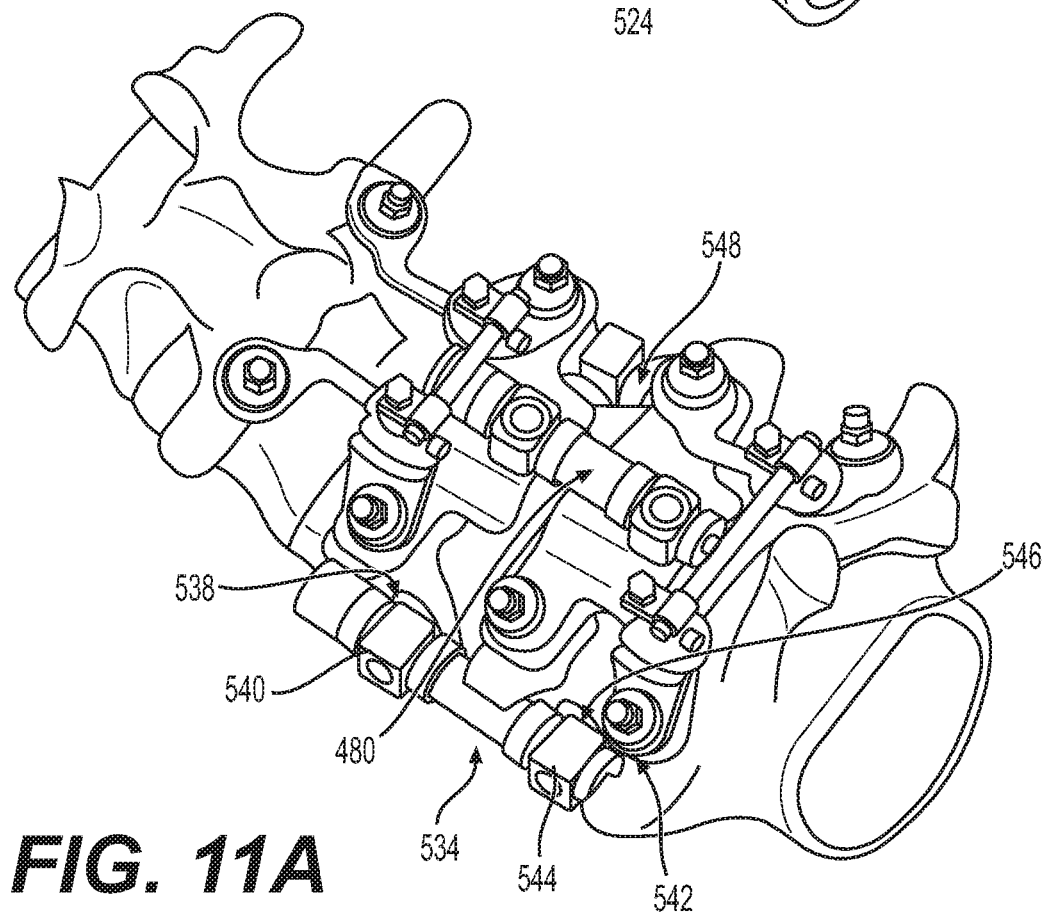
FIGS. 11A-D illustrate embodiments of bilateral stabilization assemblies of spinal implant assemblies described herein.
Figure 11B:
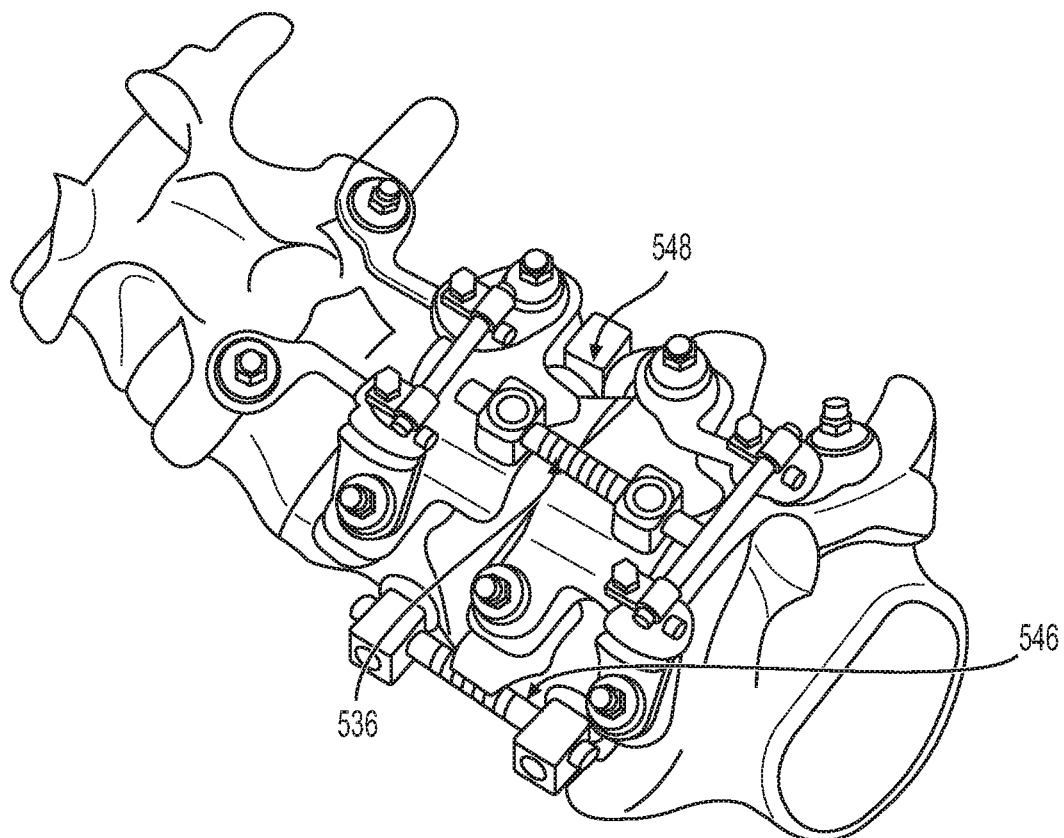

In other embodiments, the secondary stabilization system can include a bilateral stabilization assembly configured to couple two adjacent vertebrae. This assembly, which can include a left lateral assembly 546 and a right lateral assembly 548, can be configured to bilaterally couple the adjacent vertebrae directly, e.g., without coupling or attaching to the superior and/or inferior translateral stabilization systems 402, 404. In some embodiments, at least one of the left and right lateral assemblies 546, 548 can be configured to allow or promote relative motion between the two adjacent vertebrae. For example, the left lateral assembly 546 can include a dynamic connector, such as a dynamic stabilizer 534, as illustrated in FIG. 11A, or a flexible rod 536, as illustrated in FIG. 11B. The dynamic stabilizer 534 and/or the flexible rod 536 may have some or all of the same properties as the dynamic stabilizer 480 and flexible rod 482, described herein. As illustrated in FIGS. 11A-B, the left lateral assembly 546 can also include a first fixation member 538, a first housing 540, a second fixation member 542, and a second housing 544. The first and/or second fixation members 538, 542, can include, for example, a bone screw, such as a monoaxial or polyaxial screw, or other fastener. In some embodiments, the first and/or second fixation members 538, 542 can include a bone screw and a staple member. The staple member can include at least one prong or barb configured to penetrate a bone and a receiver configured to accept the bone screw therein. The first and second housings 540, 544 can each include a channel configured to receive the dynamic connector therein. Set screws can be threaded into the housings 540, 544 to secure the dynamic connector within the channels. The right lateral assembly 548 can have some or all of the same features as the left lateral assembly 546.

Figure 11C:
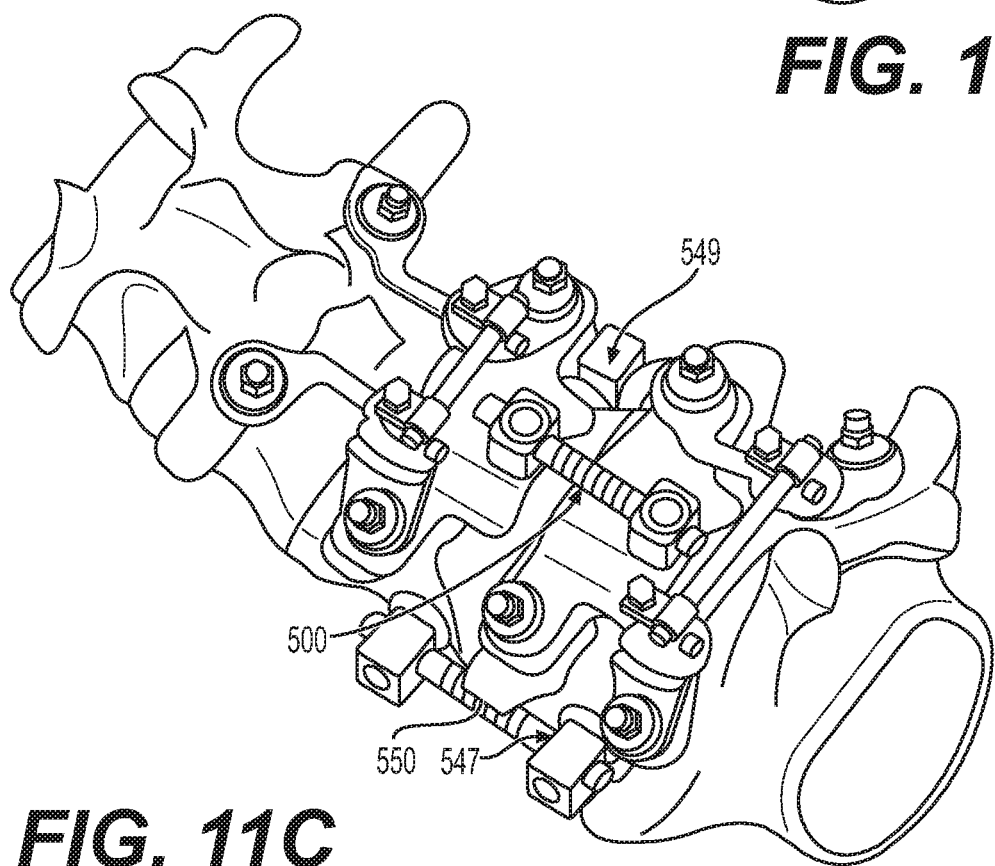
Figure 11D:
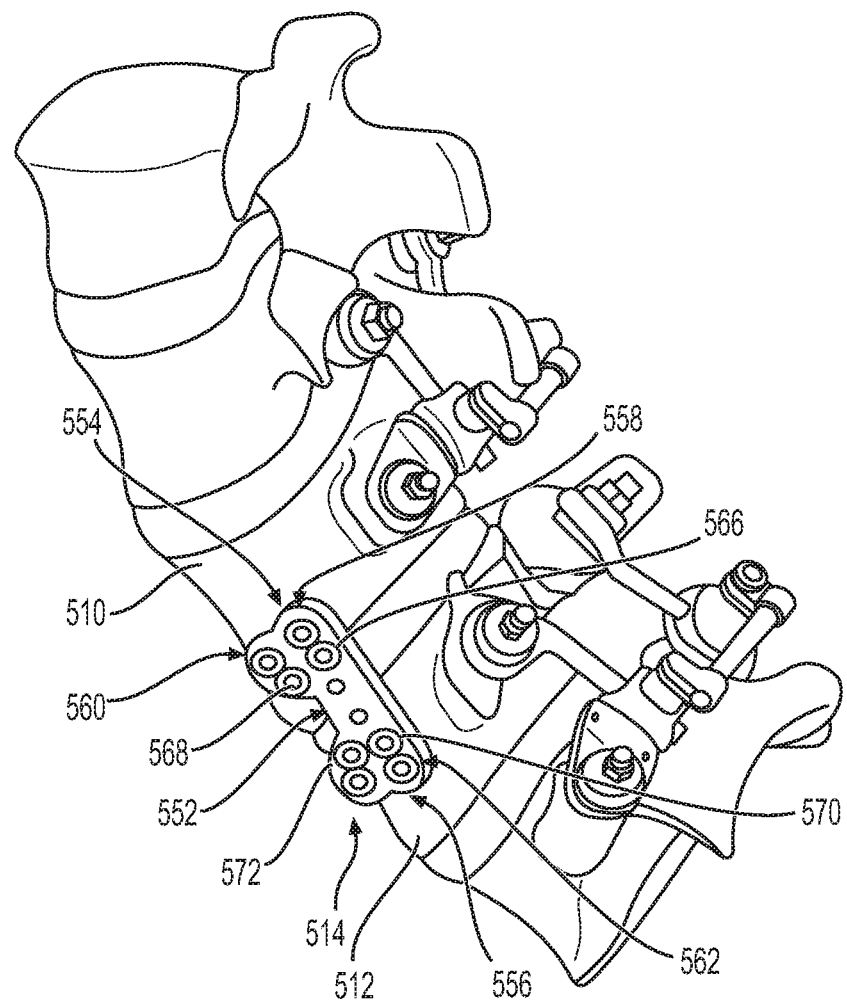

In other embodiments, at least one of the left and right lateral assemblies can be configured to prevent or inhibit relative motion between the two adjacent vertebrae. In some of these embodiments, a static connector 550 can be included, as illustrated in FIG. 11C. In other embodiments, a connecting plate 552 can be included, as illustrated in FIG. 11D. Embodiments including a static connector 550 can include left and right lateral assemblies 547, 549 having all of the same features as the left and right lateral assemblies 546, 548, except that static connector 550 can be used instead of a dynamic connector. The static connector 550 can be a rigid rod, and can have some or all of the same features as the rigid rod 500, described herein. As illustrated in FIG. 11, the static connector 550 can be configured to be received within first and second housings of the left lateral assembly 547.

In some embodiments, the left and/or right lateral assemblies 547, 549 can include a connecting plate. As illustrated in FIG. 11D, the connecting plate 552 can include a first end 554 having a bottom surface configured to contact the first, superior vertebra 510 and a second end 556 having a bottom surface configured to the contact second, inferior vertebra 512. The first and second ends 554, 556 can each have at least one bore therethrough that is configured to receive a fastener member. As illustrated in FIG. 11D, the first end 554 can include two holes 558, 560 and the second end 556 can include two holes 562, 564. One or more of the holes 558, 560, 562, 564 can include a fastener-retaining feature, such as a lock 566, 568, 570, 572. In other embodiments, other plates configured to span and/or engage the adjacent vertebrae 510, 512 may be used in place of the connecting plate 552.

Those skilled in the art may appreciate that in some embodiments, a spinal implant assembly 400 can include one, two, or three secondary stabilization systems. Any combination of intervertebral members, stabilization system connectors, and/or bilateral stabilization assemblies may be used. Additionally, as discussed herein, a spinal implant assembly 400 can include one or two superior translateral stabilization systems, and one or two inferior translateral stabilization systems. Those skilled in the art may appreciate that any combination of secondary stabilization systems can be used together with any combination of superior translateral stabilization systems and/or inferior translateral stabilization systems. Advantageously, the spinal implant assemblies 400 described herein can provide versatility and can enable the formation of spinal implants that are personalized or tailored to the features of an individual spine.

In use, the spinal implant assembly 400 may be installed in a spine which has undergone a laminectomy and a facetectomy. These procedures may be performed in accordance with techniques known to those skilled in the art. As illustrated in FIG. 9, for example, a laminectomy may be performed on superior and inferior vertebrae 510, 512 and may include removing the laminae and spinous process of each vertebra. The facet joints may also be removed. A facetectomy may be performed on second superior and inferior vertebrae 509, 513, and may include removal of the inferior articular process of the superior vertebra 509 and removal of the superior articular process of the inferior vertebra 513. Those skilled in the art may appreciate that the spinal implant assembly 400 may also be used in conjunction with alternative procedures.

Some embodiments herein are directed to methods of installing the spinal implant assembly 400. These methods can include providing a spinal implant assembly 400 as described herein. The spinal implant assembly 400 may be provided in an unassembled or partially assembled configuration, and may vary depending on which particular components are used. The method can also include installing the superior translateral stabilization system. This step can include inserting or driving the fixation members of each fixation assembly 470 into a portion of each vertebra, such as the pedicle. In embodiments that include a first translateral plate 420, this plate may be coupled with the fixation members by placing the exposed portions of the fixation members within the holes 464, 466. The base members may then be placed on the fixation members, and the split spheres 472 may be placed on the base members. In embodiments that include a first facet stabilization device 408, the method can also include coupling the left and right superior facet joint prostheses 414, 418 by placing the rings over the split spheres 472. The left and right inferior joint prostheses 412, 416 can also be coupled to the construct by placing the rings of the inferior struts over the split spheres 472. The fixation assemblies 470 may then be locked by coupling each top nut 474 with a fixation member. The crosslink rod 409 may then be coupled with the attachment mechanism 415. In some embodiments, the crosslink rod 409 may be coupled with the attachment mechanism 415 before the fixation assemblies 470 are locked. The inferior translateral stabilization system 404 can then be installed, in vertebrae 512, 513, for example, in the same way as described herein with respect to the superior translateral stabilization system 402. Those skilled in the art may appreciate that the order of these steps can be varied, and for example, the inferior translateral stabilization system 404 may be installed prior to the installation of the superior translateral stabilization system 402.

Methods herein can also include the step of installing the secondary stabilization system 406 (e.g., intervertebral member, stabilization system connector, and/or bilateral stabilization assembly). In embodiments including an intervertebral member, the intervertebral members may be installed, e.g., between vertebrae 510, 512, using techniques known to those skilled in the art. In some embodiments, the intervertebral member may be installed prior to the installation of the superior and inferior translateral stabilization systems 402, 404.

In embodiments including a stabilization system connector, this step can include coupling the stabilization system connector with the superior and inferior translateral stabilization systems 402, 404. Generally, the stabilization system connectors (e.g., dynamic stabilizer 480, flexible rod 482, and/or rigid rod 500) can be coupled to the superior translateral stabilization system 402 by inserting the stabilization system connector into the rod-receiving member 430 on the first translateral plate 420 (or rod-receiving member 431 on the first translateral plate 421) and threading the set screw 440 into the rod-receiving member 430. The stabilization system connector can be coupled to the inferior translateral stabilization system 404 in the same way. In some embodiments, the stabilization system connectors may be installed prior to the installation of the crosslink rod 409. In embodiments that include first and second connecting plates 502, 504, these elements can be coupled with the fixation members (e.g., by placing the exposed portion of each fixation member in the holes 514, 516) after the fixation members have been inserted in the vertebrae and before the other components of the fixation assembly 470 are added. In embodiments that further include the prosthetic spinous process, the method can further include coupling the prosthetic spinous process to the first and second connecting plates 502, 504, e.g., by engaging the holes of prosthetic spinous process 506 with the fastener member 530 and threading the nut 532 onto the fastener member 530.

In embodiments including a bilateral stabilization assembly having a rod-type member (e.g. dynamic stabilizer 534, flexible rod 536, and/or static connector 550), the method of installation can include coupling the left lateral assembly 546 with vertebrae 510, 512. The left lateral assembly 546 can be coupled with a left anterior or anterolateral section of each vertebrae 510, 512. This step can include inserting the first fixation member 538 into the superior vertebra 510 and inserting the second fixation member 542 into the inferior vertebra 512. The first and second housings 540, 544 may be coupled with the fixation members 538, 542 either before or after insertion of the fixation members 538, 542 into the vertebrae 510, 512. The rod-type member (e.g. dynamic stabilizer 534, flexible rod 536, and/or static connector 550) may then be placed in the channels of the housings 540, 544 and secured therein by threading set screws into the housings 540, 544. In embodiments including a bilateral stabilization assembly having a plate-type member (e.g., connecting plate 552), the method of coupling the left lateral assembly 547 can include positioning the first end 554 on the superior vertebra 510 and the second end 556 on the inferior vertebra 512. The method can also include inserting fastener members into the holes 558, 560, 562, 564 and driving them into the vertebrae. The method can further include engaging the fastener-retaining feature, e.g., by rotating the locks 566, 568, 570, 572. In any of these embodiments, the right lateral assembly 548 or 549 can be installed in the same way as the left lateral assembly 546 or 547, and can be coupled with a right anterior or anterolateral section of each vertebra 510, 512.

Any of the constructs described above can be used on their own, or in combination with one another, as well as with other implants. The constructs can be used in particular as part of a stabilization system including rods, screws (e.g., polyaxial, monoaxial, uniplanar) and plates. In addition, they can be used as part of a system including additional implants, including prosthetic devices (such as artificial discs), as well as fusion devices, such as spacers or cages that are designed to receive graft material therein. Such spacers or cages can include implants of fixed height or of adjustable height.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims. Although individual embodiments are discussed herein, the invention covers all combinations of all those embodiments.

What is claimed is:

1. A spinal implant assembly comprising:
   a first translateral plate comprising a first bone fixation assembly, a second bone fixation assembly, and a first rod receiving member, wherein the first rod receiving member includes a partially spherical concave depression and the first translateral plate includes a top surface having a partially spherical convex protrusion configured to nest with the partially spherical concave depression, thereby allowing the first rod receiving member and the first translateral plate to pivot with respect to one another, wherein the first translateral plate includes a pair of side rails disposed on either side of the partially spherical convex protrusion, wherein each side rail of the pair of side rails attaches to the top surface of the first translateral plate at two attachment points creating a window therebetween overlapping a bottom extension of the first rod receiving member;
   a second translateral plate comprising a third bone fixation assembly, a fourth bone fixation assembly and a second rod receiving member; and
   an elongated rod being received by the first rod receiving member and the second rod receiving member,
   wherein the first and second translateral plates are configured to be positioned over the lamina of adjacent vertebral bodies.

2. The spinal implant assembly of claim 1, wherein the first bone fixation assembly includes a bone anchor and a bone anchor receiving member.

3. The spinal implant assembly of claim 1, wherein the first bone fixation assembly and the second bone fixation assembly are positioned on opposing distal portions of the first translateral plate.

4. The spinal implant assembly of claim 1, wherein the first rod receiving member is positioned between the first bone fixation assembly and the second bone fixation assembly.

5. The spinal implant assembly of claim 1, wherein the first rod receiving member and the second rod receiving member are configured to receive a rod, and, further comprising an interiorly-threaded upper section.

6. The spinal implant assembly of claim 1, wherein the first and second translateral plate are contoured to be affixed to bone.

7. The spinal implant assembly of claim 1 further comprising a first facet stabilization device coupled to the first translateral plate and a second facet stabilization device coupled to the second translateral plate.

8. The spinal implant assembly of claim 7, wherein the first facet stabilization device includes a first cross link rod, and the second facet stabilization device includes a second cross link rod.

9. A spinal implant assembly comprising:
   a superior translateral stabilization system comprising a first stabilization device, a first translateral plate, and a first receiving member, wherein the first receiving member includes a partially spherical concave depression and the first translateral plate includes a top surface having a partially spherical convex protrusion configured to nest with the partially spherical concave depression, thereby allowing the first receiving member and the first translateral plate to pivot with respect to one another, wherein the first translateral plate includes a pair of side rails disposed on either side of the partially spherical convex protrusion, wherein each side rail of the pair of side rails attaches to the top surface of the first translateral plate at two attachment points creating a window therebetween overlapping a bottom extension of the first rod receiving member;
   an inferior translateral stabilization system comprising a second stabilization device and a second translateral plate; and
   a secondary stabilization system configured to couple with the first and second translateral plates and configured to couple two adjacent vertebrae.

10. The spinal implant assembly of claim 9, wherein the secondary stabilization system comprises a dynamic stabilizer.

11. The spinal implant assembly of claim 9, wherein the secondary stabilization system comprises a flexible rod.

12. The spinal implant assembly of claim 9, wherein the secondary stabilization system comprises a rigid rod made of a material selected from the group consisting of titanium and PEEK.

13. The spinal implant assembly of claim 9, wherein the secondary stabilization system comprises first and second connecting plates.

14. The spinal implant assembly of claim 9, wherein the secondary stabilization system further comprises a prosthetic spinous process.

15. A spinal implant assembly comprising:
   a first translateral plate comprising a first bone fixation assembly, a second bone fixation assembly, and a first rod receiving member, wherein the first rod receiving member includes a partially spherical concave depression and the first translateral plate includes a top surface having a partially spherical convex protrusion configured to nest with the partially spherical concave depression, thereby allowing the first rod receiving member and the first translateral plate to pivot with respect to one another, wherein the first translateral plate includes a pair of side rails disposed on either side of the partially spherical convex protrusion, wherein each side rail of the pair of side rails attaches to the top surface of the first translateral plate at two attachment points creating a window therebetween overlapping a bottom extension of the first rod receiving member;
   a second translateral plate comprising a third bone fixation assembly, a fourth bone fixation assembly and a second rod receiving member; and
   an elongated rod being received by the first rod receiving member and the second rod receiving member,
   wherein the first and second translateral plates are configured to be positioned over the lamina of adjacent vertebral bodies, wherein the first rod receiving member and the second rod receiving member comprise a u-shaped channel for receiving the elongated rod.

16. The spinal implant assembly of claim 15, wherein the first bone fixation assembly includes a bone anchor and a bone anchor receiving member.

17. The spinal implant assembly of claim 15, wherein the first bone fixation assembly and the second bone fixation assembly are positioned on opposing distal portions of the first translateral plate.

18. The spinal implant assembly of claim 15, wherein the first rod receiving member is positioned between the first bone fixation assembly and the second bone fixation assembly.

19. The spinal implant assembly of claim 15, wherein the first and second translateral plates are contoured to be affixed to bone.

\* \* \* \* \*